(12) United States Patent
Davies et al.

(10) Patent No.: US 7,663,020 B2
(45) Date of Patent: Feb. 16, 2010

(54) GENERATION OF PLANTS WITH ALTERED OIL CONTENT

(75) Inventors: John P. Davies, Portland, OR (US); Hein Tsoeng (Medard) Ng, Charlottesville, VA (US)

(73) Assignee: Agrinomics LLC, Portland, OR (US)

( * ) Notice: Subject to any disclaimer, the term of this patent is extended or adjusted under 35 U.S.C. 154(b) by 0 days.

(21) Appl. No.: 11/813,858

(22) PCT Filed: Jan. 11, 2006

(86) PCT No.: PCT/US2006/001280

§ 371 (c)(1),
(2), (4) Date: Jul. 12, 2007

(87) PCT Pub. No.: WO2006/076596

PCT Pub. Date: Jul. 20, 2006

(65) Prior Publication Data

US 2008/0124444 A1    May 29, 2008

Related U.S. Application Data

(60) Provisional application No. 60/643,674, filed on Jan. 12, 2005.

(51) Int. Cl.
*C12N 15/82* (2006.01)
*C12N 15/87* (2006.01)
*A01H 1/00* (2006.01)
*A01H 5/00* (2006.01)
*C12N 5/14* (2006.01)
*C12N 15/63* (2006.01)
*C07H 21/00* (2006.01)

(52) U.S. Cl. .................. 800/281; 800/278; 435/468
(58) Field of Classification Search .................. None
See application file for complete search history.

(56) References Cited

U.S. PATENT DOCUMENTS

| | | | |
|---|---|---|---|
| 5,322,783 | A | 6/1994 | Tomes et al. |
| 5,538,880 | A | 7/1996 | Lundquist et al. |
| 5,550,318 | A | 8/1996 | Adams et al. |
| 5,563,055 | A | 10/1996 | Townsend et al. |
| 5,610,042 | A | 3/1997 | Chang et al. |
| 5,639,790 | A | 6/1997 | Voelker et al. |
| 5,704,160 | A | 1/1998 | Bergquist et al. |
| 5,952,544 | A | 9/1999 | Browse et al. |
| 6,229,033 | B1 | 5/2001 | Knowlton |
| 6,248,939 | B1 | 6/2001 | Leto et al. |
| 2004/0025202 | A1* | 2/2004 | Laurie et al. .............. 800/281 |
| 2006/0150283 | A1* | 7/2006 | Alexandrov et al. ........ 800/288 |
| 2006/0277630 | A1 | 12/2006 | Lightner et al. |

FOREIGN PATENT DOCUMENTS

| | | | |
|---|---|---|---|
| EP | 1 033 405 A2 | | 9/2000 |
| EP | 1033405 A2 | * | 9/2000 |
| WO | WO 94/11516 | | 5/1994 |
| WO | WO 95/06128 | | 3/1995 |
| WO | WO01/83697 | | 11/2001 |
| WO | WO 03/02751 A2 | * | 9/2003 |
| WO | WO 2004/093528 A2 | | 11/2004 |
| WO | WO 2004/093532 A2 | | 11/2004 |
| WO | WO 2005/107437 | | 11/2005 |
| WO | WO 2007/053482 | | 5/2007 |

OTHER PUBLICATIONS

Zou et al. (The Plant Cell, 9:909-923, 1997).*
Jako et al. (Plant Physiol. 126:861-874, 2001).*
Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Wells, (Biochemistry 29:8509-8517, 1990).*
Ngo et al., (The Protein Folding Problem and Tertiary Structure Prediction, K. Merz., and S. Le Grand (eds.) pp. 492-495,1994).*
Doerks et al., (TIG, 14:248-250, 1998).*
Smith et al. (Nature Biotechnology, 15:1222-1223, 1997).*
Bork et al. (TIG, 12:425-427, 1996).*
Broun et al. (Science, 282:1315-1317, 1998).*
Shinn et al., EMBL Database Accession No. AY070479, Dec. 28, 2001 (2 pages).
Bateman et al., "Pfam 3.1: 1313 multiple alignments and profile HMMs match the majority of proteins," *Nucleic Acids Research*, 27:260-262 (1999).
Browse et al., "Fluxes through the prokaryotic and eukaryotic pathways of lipid synthesis in the '16:3' plant *Arabidopsis thaliana*," *Biochem J.*, 235:25-31 (1986).
Chapple and Carpita, "Plant cell walls as targets for biotechnology," *Current Opinion in Plant Biology*, 1:179-185 (1998).
Christensen et al., *9th International Conference Arabidopsis Research*, Univ. of Wisconsin-Madison, Jun. 24-28, Abstract 165 (1998).
Christou et al., "Inheritance and expression of foreign genes in transgenic soybean plants," *Proc. Natl. Acad. Sci. USA*, 86:7500-7504 (1989).
DeBlock et al., "Transformation of *Brassica napus* and *Brassica oleracea* Using *Agrobacterium tumefaciens* and the Expression of the *bar* and *neo* Genes in the Transgeneic Plants," *Plant Physiology*, 91:694-701 (1989).
Douglas et al., "Nutritional evaluation of low phytate and high protein corns," *Poultry Science*, 79:1586-1591 (2000).
Edwards et al., "Protein and energy evaluation of soybean meals processed from genetically modified high-protein soybeans," *Poultry Science*, 79:525-527 (1999).
Everett et al., "Genetic engineering of sunflower (*Helianthus annus* L.)," *Bio/Technology*, 5:1201 (1987).
Falco et al., "Transgenic canola and soybean seeds with increased lysine," *Bio/Technology*, 13:577-582 (1995).
Fridborg et al., "The Arabidopsis dwarf mutant *shi* exhibits reduced gibberellins responses conferred by overexpression of a new putative zinc finger protein," *Plant Cell*, 11:1019-1032 (1999).

(Continued)

*Primary Examiner*—Vinod Kumar
(74) *Attorney, Agent, or Firm*—Klarquist Sparkman, LLP.

(57) ABSTRACT

The present disclosure is directed to plants and plant cells that display an altered oil content phenotype due to altered expression of a HIO nucleic acid. The disclosure is further directed to methods of generating plants with an altered oil content phenotype.

9 Claims, No Drawings

OTHER PUBLICATIONS

Hayashi et al., "Activation of a plant gene by T-DNA tagging: auxin-independent growth in vitro," *Science*, 258:1350-1353 (1992).
Honig and Rackis, "Determination of the total pepsin-pancreatin indigestible content (dietary fiber) of soybean products, wheat bran, and corn bran," *J. Agri. Food Chem.*, 27:1262-1266 (1979).
Kardailsky et al., "Activation tagging of the floral inducer FT," *Science*, 286:1962-1965 (1999).
Klein et al., "High velocity microprojectiles for delivering nucleic acids into living cells," *Nature*, 327:70-73 (1987).
Moore et al., "Chromatography of Amino Acids on Sulfonated Polystyrene Resins," *Anal. Chem.*, 30:1185-1190 (1958).
Mulder et al., "The InterPro Database, 2003 brings increased coverage and new features," *Nucleic Acids Res.*, 31:315-318 (2003).
Parsons et al., "Nutritional evaluation of soybean meals varying in oligosaccharide content," *Poultry Sci.*, 79:1127-1131 (2000).
Schaffer et al., "*The late elongated hypocotyl* mutation of *Arabidopsis* disrupts circadin rhythms and the photoperiodic control of flowering," *Cell*, 93:1219-1229 (1998).
Shewry, "Seed storage proteins: structures and biosynthesis," Plant Cell, 7:945-956 (1995).
Weigel et al., "Activation tagging in Arabidopsis," *Plant Physiology*, 122:1003-1013 (2000).
Wilson et al., "A *Dissociation* insertion causes a semidominant mutation that increases expression of *TINY*, an Arabidopsis gene related to *APETALA2*," Plant Cell, 8:659-671 (1996).
Zou et al., "Modification of Seed Oil Content and Acyl Composition in the Brassicaceae by Expression of a Yeast *sn*-2 Acyltransferase Gene," *The Plant Cell*, 9:909-923 (1997).
Anoop et al., "Modulation of citrate metabolism alters aluminum tolerance in yeast and transgenic canola overexpressing a mitochondrial citrate synthase," *Plant Physiol.*, 132:2205-2217, 2003.
Beisson et al., "Arabidopsis genes involved in acyl lipid metabolism. A 2003 census of the candidates, a study of the distribution of expressed sequence tags in organs, and a web-based database," *Plant Physiol.*, 132:681-697, 2003.
Bert et al., "Comparative genetic analysis of quantitative traits in sunflower (*Helianthus annuus* L.). 2. Characterisation of QTL involved in developmental and agronomic traits," *Theor. Appl. Genet.*, 107:181-189, 2003.
Colbert et al., "High-throughput screening for induced point mutations," *Plant Physiol.*, 126(2):480-484, 2001.
Dehesh et al., "Overexpression of 3-ketoacyl-acyl-carrier protein synthase IIIs in plants reduces the rate of lipid synthesis," *Plant Physiol.*, 125:1103-1114, 2001.
Eastmond and Graham, "Re-examining the role of glyoxylate cycle in oilseeds," *Trends Plant Sci.*, 6(2):72-77, 2001.
Eccleston and Ohlrogge, "Expressions of lauroyl-acyl carrier protein thioesterase in *Brassica napus* seeds induces pathways for both fatty acid oxidation and biosynthesis and implies a set point for triacylglycerol accumulation," *Plant Cell*. 10:613-621, 1998.
Fatland et al., "Molecular biology of cytosolic acetyl-CoA generation," *Biochem. Soc. Trans.*, 28(6):593-595, 2000.
Fatland et al., "Reverse genetic characterization of cytosolic acetyl-CoA generation by ATP-citrate lyase in Arabidopsis," *Plant Cell*, 17:182-203, 2005.
Feldmann et al., "A Dwarf Mutant of Arabidopsis Generated by T-DNA Insertion Mutagenesis," *Science*, 243(4896):1351-1354, 1989.
Focks and Benning, "*wrinkled1*: A novel, low-seed-oil mutant of Arabidopsis with a deficiency in the seed-specific regulation of carbohydrate metabolism," *Plant Physiol.*, 118:91-101, 1998.
Girke et al., "Microarray analysis of developing Arabidopsis seeds," *Plant Physiol.*, 124:1570-1581, 2000.
Jako et al., "Seed-specific over-expression of an Arabidopsis cDNA encoding a diacylglycerol acyltransferase enhances seed oil content and seed weight," *Plant Physiol.*, 126(2):861-874, 2001.
James and Dooner, "Isolation of EMS-induced mutants in Arabidopsis altered in seed fatty acid composition," *Theor. Appl. Genet.*, 80(2):241-245, 1990.

Katavic et al., "Alteration of seed fatty acid composition by an ethyl methanesulfonate-induced mutation in *Arabidopsis thaliana* affecting diacylglycerol acyltransferase activity," *Plant Physiol.*,108:399-409, 1995.
Katavic et al., "Utility of the *Arabidopsis FAE1* and yeast *SLC1-1* genes for improvements in erucic acid and oil content in rapeseed," *Biochem Soc. Trans*., 28(6):935-937, 2000.
Larson et al., "Acyl CoA profiles of transgenic plants that accumulate medium-chain fatty acids indicate inefficient storage lipid synthesis in developing oilseeds," *Plant J.*, 32:519-527, 2002.
Lemieux et al., "Mutants of Arabidopsis with alterations in seed lipid fatty acid composition," *Theor. Appl. Genet.*, 80(2):234-240, 1990.
Lin et al., "The Pex16p homolog SSE1 and storage organelle formation in *Arabidopsis* seeds," *Science*. 284:328-330, 1999.
Lionneton et al., "Development of an AFLP-based linkage map and localization of QTLs for seed fatty acid content in condiment mustard (*Brassica juncea*)," *Genome*, 45(6):1203-1215, 2002.
Liu and Butow, "A transcriptional switch in the expression of yeast tricarboxylic acid cycle genes in response to a reduction or loss of respiratory function," *Mol. Cell. Biol.*, 19:6720-6728, 1999.
Mccallum et al., "Targeted screening for induced mutations," *Nat. Biotechnol.*, 18(4):455-457, 2000.
Mekhedov et al., "Toward a functional catalog of the plant genome. A survey of genes for lipid biosynthesis," *Plant Physiol.*, 122:389-401, 2000.
Moire et al., "Impact of unusual fatty acid synthesis on futile cycling through β-oxidation and on gene expression in transgenic plants," *Plant Physiol.*, 134:432-442, 2004.
Neuhaus and Emes, "Nonphotosynthetic Metabolism In Plastids," *Annu. Rev. Plant Physiol. Plant Mol. Biol.*, 51:111-140, 2000.
O'Hara et al., "Fatty acid and lipid biosynthetic genes are expressed at constant molar ratios but different absolute levels during embryogenesis," *Plant Physiol.*, 129:310-320, 2002.
Okuley et al., "Arabidopsis FAD2 Gene Encodes the Enzyme That Is Essential for Polyunsaturated Lipid Synthesis," *Plant Cell*, 6:147-158, 1994.
Pritchard et al., "Germination and storage reserve mobilization are regulated independently in *Arabidopsis,*" *Plant J.*, 31(5):639-647, 2002.
Rangasamy and Ratledge, "Compartmentation of ATP:Citrate lyase in plants," *Plant Physiol.*, 122:1225-1230, 2000.
Rangasamy and Ratledge, "Genetic enhancement of fatty acid synthesis by targeting rat liver ATP:citrate lyase into plastids of tobacco," *Plant Physiol.*, 122:1231-1238, 2000.
Ratledge et al, "Correlation of ATP/citrate lyase activity with lipid accumulation in developing seeds of *Brassica napus* L.," *Lipids*, 32(1):7-12, 1997.
Rawsthorne, S., "Carbon flux and fatty acid synthesis in plants," *Prog Lipid Res*., 41:182-196, 2002.
Ruuska et al., "Contrapuntal networks of gene expression during Arabidopsis seed filling," *Plant Cell*, 14:1191-1206, 2002.
Rylott et al., "Co-ordinate regulation of genes involved in storage lipid mobilization in *Arabidopsis thaliana*," *Biochem Soc. Trans*., 29:283-287, 2001.
Schnarrenberger and Martin, "Evolution of the enzymes of the citric acid cycle and the glyoxylate cycle of higher plants, A case study of endosymbiotic gene transfer," *Eur. J. Biochem*., 269:868-883, 2002.
Schnurr et al., "Characterization of an acyl-CoA synthetase from *Arabidopsis thaliana*," *Biochem Soc. Trans*., 28(6):957-958, 2000.
Shockey et al., "Characterization of the AMP-binding protein gene family in *Arabidopsis thaliana*: will the real acyl-CoA synthetases please stand up?" *Biochem Soc. Trans*., 28(6):955-957, 2000.
Thelen et al., "Biotin carboxyl carrier protein isoforms in Brassicaceae oilseeds," *Biochem. Soc. Trans*., 28(6):595-598, 2000.
Wada et al., "Role of a positive regulator of root hair development, Caprice, in Arabidopsis root epidermal cell differentiation," *Development*, 129(23):5409-5419, 2002.
White et al., "A new set of Arabidopsis expressed sequence tags from developing seeds. The metabolic pathway from carbohydrates to seed oil," *Plant Physiol.*, 124:1582-1594, 2000.
Yadav et al., "Cloning of higher plant omega-3 fatty acid desaturases," *Plant Physiol.*, 103(2):467-476, 1993.

\* cited by examiner

GENERATION OF PLANTS WITH ALTERED OIL CONTENT

CROSS REFERENCE TO RELATED APPLICATIONS

This is the U.S. National Stage of International Application No. PCT/US2006/001280, filed Jan. 11, 2006, which was published in English under PCT Article 21(2), which in turn claims the benefit of U.S. Provisional Application No. 60/643,674, filed Jan. 12, 2005, the contents of both of which are hereby incorporated by reference.

FIELD OF THE DISCLOSURE

The present disclosure is related to transgenic plants and plant cells with altered oil content, as well as methods of making plants having altered oil content and producing oil from such plants.

BACKGROUND

The ability to manipulate the composition of crop seeds, particularly the content and composition of seed oils, has important applications in the agricultural industries, relating both to processed food oils and to animal feeds. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remaining seed meal is sold for livestock feed (U.S. Soybean Board, 2001 Soy Stats). Canola seed is also crushed to produce oil and the co-product canola meal (Canola Council of Canada). Nearly 20% of the 1999/2000 U.S. corn crop was industrially refined, primarily for production of starch, ethanol and oil (Corn Refiners Association). Thus, it is often desirable to maximize oil content of seeds. For instance, for processed oilseeds such as soy and canola, increasing the absolute oil content of the seed will increase the value of such grains. For processed corn it may be desired to either increase or decrease oil content, depending on utilization of other major constituents. Decreasing oil may improve the quality of isolated starch by reducing undesired flavors associated with oil oxidation. Alternatively, in ethanol production, where flavor is unimportant, increasing oil content may increase overall value.

In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors.

Biotechnological manipulation of oils can provide compositional alteration and improvement of oil yield. Compositional alterations include high oleic acid soybean and corn oil (U.S. Pat. Nos, 6,229,033 and 6,248,939), and laurate-containing seeds (U.S. Pat. No. 5,639,790), among others. Work in compositional alteration has predominantly focused on processed oilseeds, but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil content in current HOC fields has plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

The most obvious target crops for the processed oil market are soy and rapeseed, and a large body of commercial work (e.g., U.S. Pat. No. 5,952,544; PCT Application No. WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990, *Theor. Appl. Genet.* 80, 234-240; James and Dooner, 1990, *Theor. Appl. Genet.* 80, 241-245). T-DNA mutagenesis screens (Feldmnann et al., 1989, *Science* 243: 1351-1354) that detected altered fatty acid composition identified the omega 3 desaturase (FAD3) and delta-12 desaturase (FAD2) genes (U.S. Pat. No. 5,952,544; Yadav et al., 1993, *Plant Physiol.* 103, 467-476; Okuley et al, 1994, *Plant Cell* 6(1):147-158). A screen which focused on oil content rather than oil quality, analyzed chemically-induced mutants for wrinkled seeds or altered seed density, from which altered seed oil content was inferred (Focks and Benning, 1998, Plant Physiol 118:91-101).

Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al., 1995, *Plant Physiol.* 108(1):399-409). It was further shown that seed-specific over-expression of the DGAT cDNA was associated with increased seed oil content (Jako et al, 2001, *Plant Physiol.* 126(2):861-74). *Arabidopsis* is also a model for understanding the accumulation of seed components that affect meal quality. For example, *Arabidopsis* contains albumin and globulin seed storage proteins found in many dicotyledonous plants including canola and soybean (Shewry 1995, *Plant Cell* 7:945-956). The biochemical pathways for synthesizing components of fiber, such as cellulose and lignin, are conserved within the vascular plants, and mutants of *Arabidopsis* affecting these components have been isolated (reviewed in Chapel and Carpita 1998, *Current Opinion in Plant Biology* 1:179-185).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992, *Science* 258: 1350-1353; Weigel D et al., 2000, *Plant Physiology*, 122:1003-1013). The inserted construct provides a molecular tag for rapid identification of the native plant whose mis-expression causes the mutant phenotype Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, *Plant Cell* 8: 659-671; Schaffer et al, 1998, *Cell* 93: 1219-1229; Fridborg et al., 1999, *Plant Cell* 11: 1019-1032; Kardailsky et al., 1999, *Science* 286: 1962-1965; and Christensen S et al., 1998, 9$^{th}$ *International Conference on Arabidopsis Research*, Univ. of Wisconsin-Madison, June 24-28, Abstract 165).

SUMMARY

Provided herein are transgenic plants having a high oil (hereinafter "HIO") phenotype. Transgenic plants with a HIO phenotype have an altered or increased oil content in any part of the plant, for example the seeds, relative to control, non-transgenic, or wild-type plants. Further provided is oil derived from the seeds of transgenic plants, wherein the seeds have an altered or increased oil content. Also provided herein is meal, feed, or food generated from any part of a transgenic plant having a HIO phenotype.

In certain embodiments, the transgenic plant comprises a transformation vector comprising a nucleotide sequence that encodes or is complementary to a sequence that encodes a HIO polypeptide. In particular embodiments, expression of a HIO polypeptide in a transgenic plant causes an altered or increased oil content in the transgenic plant. In preferred embodiments, the transgenic plant is selected from the group consisting of rapeseed, soy, corn, sunflower, cotton, cocoa, safflower, oil palm, coconut palm, flax, castor and peanut. The disclosure further provides a method of producing oil comprising growing the transgenic plant and recovering oil from said plant. The disclosure further provides feed, meal, grain, or seed comprising a nucleic acid sequence that encodes a HIO polypeptide. The disclosure also provides feed, meal, grain, or seed comprising the HIO polypeptide or an ortholog thereof.

The disclosed transgenic plants are produced by a method that comprises introducing into progenitor cells of the plant a plant transformation vector comprising a nucleotide sequence that encodes or is complementary to a sequence that encodes a HIO polypeptide, and growing the transformed progenitor cells to produce a transgenic plant, wherein the HIO polynucleotide sequence is expressed causing the high oil phenotype in the transgenic plant In other embodiments, the disclosed transgenic plant is the direct progeny or the indirect progeny of a plant grown from said progenitor cells. In specific, non-limiting examples, the method produces transgenic plants wherein expression of the HIO polypeptide causes a HIO phenotype in the transgenic plant, relative to control, non-transgenic, or wild-type plants.

Additional methods are disclosed herein of generating a plant having a HIO phenotype, wherein a plant is identified that has an allele in its HIO nucleic acid sequence that results in a HIO phenotype, compared to plants lacking the allele. The plant can generate progeny, wherein the progeny inherit the allele and have a HIO phenotype. In some embodiments of the method, the method employs candidate gene/QTL methodology or TILLING methodology.

Also provided herein is a transgenic plant cell having a HIO phenotype. The transgenic plant cell comprises a transformation vector comprising a HIO nucleotide sequence that encodes or is complementary to a sequence that encodes a HIO polypeptide. In preferred embodiments, the transgenic plant cell is selected from the group consisting of canola, rapeseed, soy, corn, sunflower, cotton, cocoa, safflower, oil palm, coconut palm, flax, castor, and peanut. In other embodiments, the plant cell is a seed, pollen, propagule, or embryo cell. In some embodiments, the plant cells are obtained from the disclosed transgenic plant. The disclosure also provides plant cells from a plant that is the direct progeny or the indirect progeny of a plant grown from said progenitor cells, or plant cells from a plant that is the direct progeny or the indirect progeny of a plant grown from said progenitor cells.

The present disclosure also provides a container of over about 10,000, more preferably about 20,000, and even more preferably about 40,000 seeds where over about 10%, more preferably about 25%, more preferably about 50%, and even more preferably about 75% or more preferably about 90% of the seeds are seeds derived from a plant of the present disclosure.

The present disclosure also provides a container of over about 10 kg, more preferably about 25 kg, and even more preferably about 50 kg seeds where over about 10%, more preferably about 25%, more preferably about 50% and even more preferably about 75% or more preferably about 90% of the seeds are seeds derived from a plant of the present disclosure.

Any of the plants or parts thereof of the present disclosure may be processed to produce a feed, food, meal, or oil preparation. A particularly preferred plant part for this purpose is a seed. In a preferred embodiment the feed, food, meal, or oil preparation is designed for animals. Methods to produce feed, food, meal, and oil preparations are known in the art. See, for example, U.S. Pat. Nos. 4,957,748; 5,100,679; 5,219,596; 5,936,069; 6,005,076; 6,146,669; and 6,156,227. The meal of the present disclosure may be blended with other meals. In a preferred embodiment, the meal produced from plants of the present disclosure or generated by a method of the present disclosure constitutes greater than about 0.5%, about 1%, about 5%, about 10%, about 25%, about 50%, about 75%, or about 90% by volume or weight of the meal component of any product. In another embodiment, the meal preparation may be blended and can constitute greater than about 10%, about 25%, about 35%, about 50%, or about 75% of the blend by volume.

DETAILED DESCRIPTION

Terms

Unless otherwise indicated, all technical and scientific terms used herein have the same meaning as they would to one skilled in the art of the present disclosure. Practitioners are particularly directed to Sambrook et al., 1989, and Ausubel FM et al., 1993, for definitions and terms of the art. It is to be understood that this disclosure is not limited to the particular methodology, protocols, and reagents described, as these may vary.

As used herein, the term "high oil (HIO) phenotype" refers to plants, or any part of a plant (for example, seeds), with an altered oil content (phenotype). As provided herein, altered oil content includes an increased oil content in plants or seeds, compared to a control, non-transgenic, or wildtype plant.

As used herein, the term "content" refers to the type and relative amount of, for instance, a seed or seed meal component.

As used herein, the term "meal" refers to seed components remaining following the extraction of oil from the seed. Examples of components of meal include protein and fiber.

As used herein, the term "fiber" refers to non-digestible components of the plant seed including cellular components such as cellulose, hemicellulose, pectin, lignin, and phenolics.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell by infection, transfection, microinjection, electroporation, or the like. A "heterologous" nucleic acid construct may contain a control sequence/DNA coding sequence combination that is the same as, or different from, a control sequence/DNA coding sequence combination found in the native plant. Specific, non-limiting examples of a heterologous nucleic acid sequence include a HIO nucleic acid sequence, or a fragment, derivative (variant), or ortholog thereof.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequences.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or id-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, includes "transfection," "transformation," and "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g. callus), as well as any type of cell that is found in a seed, a pollen grain, a propagule, or an embryo, or a structure associated therewith.

As used herein, the terms "native" and "wild-type" relative to a given plant trait or phenotype refers to the form in which that trait or phenotype is found in the same variety of plant in nature. In one embodiment, a wild-type plant is also a control plant. In another embodiment, a wildtype plant is a non-transgenic plant.

As used herein, the term "modified" regarding a plant trait, refers to a change in the phenotype of a transgenic plant (for example, a transgenic plant with an altered oil content) in any part of the transgenic plant, for example the seeds, relative to a similar non-transgenic plant. As used herein, the term "altered" refers to either an increase or a decrease of a plant trait or phenotype (for example, oil content) in a transgenic plant, relative to a similar non-transgenic plant. In one specific, non-limiting example, a transgenic plant with a modified trait includes a plant with an increased oil content, or HIO content, relative to a similar non-transgenic plant.

An "interesting phenotype (trait)" with reference to a transgenic plant refers to an observable or measurable phenotype demonstrated by a T1 and/or subsequent generation plant, which is not displayed by the corresponding non-transgenic plant (i.e., a genotypically similar plant that has been raised or assayed under similar conditions). An interesting phenotype may represent an improvement in the plant (for example, increased oil content or HIO content in seeds of the plant) or may provide a means to produce improvements in other plants. An "improvement" is a feature that may enhance the utility of a plant species or variety by providing the plant with a unique and/or novel phenotype or quality. Such transgenic plants may have an improved phenotype, such as an HIO phenotype.

The phrase "altered oil content phenotype" refers to a measurable phenotype of a genetically modified (transgenic) plant, where the plant displays a statistically significant increase or decrease in overall oil content (i.e., the percentage of seed mass that is oil), as compared to the similar, but non-modified (non-transgenic) plant. A high oil (HIO) phenotype refers to an increase in overall oil content.

As used herein, a "mutant" polynucleotide sequence or gene differs from the corresponding wild-type polynucleotide sequence or gene either in terms of sequence or expression, where the difference contributes to a modified or altered plant phenotype or trait. Relative to a plant or plant line, the term "mutant" refers to a plant or plant line which has a modified or altered plant phenotype or trait, where the modified or altered phenotype or trait is associated with the modified or altered expression of a wild-type polynucleotide sequence or gene.

As used herein, the term "T1" refers to the generation of plants from the seed of T0 plants. The T1 generation is the first set of transformed plants that can be selected by application of a selection agent, e.g. an antibiotic or herbicide, for which the transgenic plant contains the corresponding resistance gene. The term "T2" refers to the generation of plants by self-fertilization of the flowers of T1 plants, previously selected as being transgenic T3 plants are generated from T2 plants, etc.

As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. Provided herein is a transgenic plant cell having a HIO phenotype. The transgenic plant cell comprises a transformation vector comprising a HIO nucleotide sequence that encodes or is complementary to a sequence that encodes a HIO polypeptide. In preferred embodiments, the transgenic plant cell is of a plant selected from the group consisting of canola, rapeseed, soy, corn, sunflower, cotton, cocoa, safflower, oil palm, coconut palm, flax, castor, and peanut. In other embodiments, the plant cell is a seed, pollen, propagule, or embryo cell, including any type of cell that is found in a seed, a pollen grain, a propagule, or an embryo, or a structure associated therewith. The disclosure also provides plant cells from a plant that is the direct progeny or the indirect progeny of a plant grown from said progenitor cells. The class of plants which can be used in the methods of the present disclosure is generally as broad as the class of higher plants amenable to transformation techniques, including both monocotyledonous and dicotyledonous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present disclosure is stably integrated into the genome such that the polynucleotide is passed on to successive generations. A plant cell, tissue, organ, or plant into which the heterologous polynucleotides have been introduced is considered "transformed," "transfected," or "transgenic." Direct and indirect progeny of transformed plants or plant cells that also contain the heterologous polynucleotide are also considered transgenic.

Disclosed herein are transgenic plants having a HIO phenotype. Transgenic plants with a HIO phenotype may include an improved oil quantity or an altered oil content in any part of the transgenic plant, for example in the seeds. Also provided is oil derived from the seeds of transgenic plants, wherein the seeds have altered oil content. Further provided herein is meal, feed, or food produced from any part of the transgenic plant with a HIO phenotype.

In certain embodiments, the disclosed transgenic plants comprise a transformation vector comprising a HIO nucleotide sequence that encodes or is complementary to a sequence that encodes a "HIO" polypeptide. In particular embodiments, expression of a HIO polypeptide in a transgenic plant causes an altered oil content in the transgenic plant. In preferred embodiments, the transgenic plant is selected from the group consisting of canola, rapeseed, soy, corn, sunflower, cotton, cocoa, safflower, oil palm, coconut palm, flax, castor, and peanut. Also provided is a method of producing oil or seed meal, comprising growing the transgenic plant and recovering oil and/or seed meal from said plant. The disclosure further provides feed, meal, grain, or seed comprising a nucleic acid sequence that encodes a HIO polypeptide. The disclosure also provides feed, meal, grain, or seed comprising the HIO polypeptide, or an ortholog thereof.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e. the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation." Following the inoculation, the *Agrobacterium* and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. Nos. 5,550,318; 5,538,880, 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication No. WO 95/06128), barley, wheat (U.S. Pat. No. 5,563,055, incorporated herein by reference in its entirety), rice, oat, rye, sugarcane, and sorghum, as well as a number of dicots including tobacco, soybean U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin), methotrexate (and trimethoprim), chloramphenicol, and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. Nos. 5,627,061, 5,633,435, and 6,040,497 and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucteotide molecule encoding phytoene desaturase (crtI) described in Misawa et al, (Plant J. 4:833-840, 1993) and Misawa et al., (*Plant J* 6:481-489, 1994) for norflurazon tolerance; a polynucleotide molecule encoding acetohydroxyacid synthase (AHAS, also known as ALS) described in Sathasiivan et al (*Nucl. Acids Res.* 18:2188-2193, 1990) for tolerance to sulfonylurea herbicides; and the bar gene described in DeBlock, et al., (*EMBO J.* 6:2513-2519, 1987) for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafer planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present disclosure can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with a Altered Oil Content Phenotype

An *Arabidopsis* activation tagging (ACTTAG) screen was used to identify the association between the genes identified and designated HIO# (listed in column 1 of Table 1 below) and altered oil content phenotypes (specifically, high oil phenotypes). Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al., 2000). When the T-DNA inserts into the genome of transformed plants, the enhancer element can cause up-regulation genes in the vicinity, generally within about 10 kilobase (kb) of the enhancer. T1 plants were exposed to the selective agent in order to specifically recover transformed plants. To amplify the seed stocks, about eighteen T2 seed from each T1 plant were sown in soil and, after germination, exposed to the selective agent to recover transformed T2 plants. T3 seed from these plants was harvested and pooled. Oil content was estimated using one of two methods; measurement of fatty acid content and composition in T2 seeds using Gas Chromatography (GC) for HIO30.1 or estimation of total lipid content of T3 seeds using NIR infrared Spectroscopy (NIR) for HIO101B.

The association of the HIO nucleic acid with the high oil phenotype was discovered by analysis of the genomic DNA sequence flanking the T-DNA insertion in the identified line. Accordingly, HIO nucleic acids and/or polypeptides may be employed in the development of genetically modified plants having a modified oil content phenotype ("a HIO phenotype"). HIO nucleic acids may be used in the generation of oilseed crops that provide improved oil yield from oilseed processing and in the generation of feed grain crops that provide increased energy for animal feeding. HIO nucleic acids may further be used to increase the oil content of specialty oil crops, in order to augment yield of desired unusual fatty acids. Transgenic plants that have been genetically modified to express HIO polypeptides can be used in the production of oil, wherein the transgenic plants are grown, and oil is obtained from plant parts (e.g. seed) using standard methods.

HIO Nucleic Acids and Polypeptides

The HIO nucleic acids discovered in the activation tagging screen are listed in column 1 of Table 1. The *Arabidopsis* Information Resource (TAIR) identification numbers are provided in column 2. Columns 3-4 provide Genbank identifier numbers (GI#s) for the nucleotide and polypeptide sequences, respectively. Column 5 lists the putative biochemical function and/or protein name. Column 6 lists conserved protein domains. Column 7 lists the relative seed oil content of plants over-expressing the HIO nucleic acid. Column 8 provides GI#s for nucleic acid and/or polypeptide sequences of orthologous genes from other plant species.

Arabidopsis HIO30.1 nucleic acid (genomic DNA) sequence is provided in SEQ ID NO: 1 and in GenBank entry GI#30694055. The corresponding protein sequence is provided in SEQ ID NO: 2 and in GI#15232503. Arabidopsis HIO101B nucleic acid is provided in SEQ ID NO: 3 and in GenBank entry GI#30680675. The corresponding protein sequence is provided in SEQ ID NO: 4 and in GI#30680676.

As used herein, the term "HIO polypeptide" refers to any polypeptide that when expressed in a plant causes a HIO phenotype in any part of the plant, for example the seeds. The present disclosure also provides a container of over about 10,000, more preferably about 20,000, and even more preferably about 40,000 seeds where over about 10%, more preferably about 25%, more preferably about 50%, and even more preferably about 75% or more preferably about 90% of the seeds are seeds derived from a plant of the present disclosure.

The present disclosure also provides a container of over about 11 kg, more preferably about 25 kg, and even more preferably about 50 kg seeds where over about 10%, more preferably about 25%, more preferably about 50%, and even more preferably about 75% or more preferably about 90% of the seeds are seeds derived from a plant of the present disclosure.

As used herein, the term "HIO polypeptide" refers to a full-length HIO protein or a fragment, derivative (variant), or ortholog thereof that is "functionally active," such that the protein fragment, derivative, or ortholog exhibits one or more or the functional activities associated with the full-length HIO polypeptide. In one preferred embodiment, a functionally active HIO polypeptide causes a HIO phenotype in a transgenic plant. In one preferred embodiment, a functionally active HIO polypeptide causes an altered oil content phenotype when mis-expressed in a plant. In a further preferred embodiment, mis-expression of the HIO polypeptide causes a high oil phenotype in a plant. In another embodiment, a functionally active HIO polypeptide is capable of rescuing defective (including deficient) endogenous HIO activity when expressed in a plant or in plant cells; the rescuing polypeptide may be from the same or from a different species as that with defective activity. In another embodiment, a functionally active fragment of a full length HIO polypeptide retains one of more of the biological properties associated with the full-length HIO polypeptide, such as signaling activity, binding activity, catalytic activity, or cellular or extracellular localizing activity.

A HIO fragment preferably comprises a HIO domain, such as a C- or N-terminal or catalytic domain, among others, and preferably comprises at least 10, preferably at least 20, more preferably at least 25, and most preferably at least 50 contiguous amino acids of a HIO protein. Functional domains of HIO genes are listed in column 6 of Table 1 and can be identified using the PFAM program (Bateman A et al., 1999 Nucleic Acids Res. 27:260-262) or INTERPRO (Mulder et al., 2003, Nucleic Acids Res. 31, 315-318) program. Functionally active variants of full-length HIO polypeptides, or fragments thereof, include polypeptides with amino acid insertions, deletions, or substitutions that retain one of more of the biological properties associated with the full-length HIO polypeptide. In some cases, variants are generated that change the post-translational processing of a HIO polypeptide. For instance, variants may have altered protein transport or protein localization characteristics, or altered protein half-life, compared to the native polypeptide.

As used herein, the term "HIO nucleic acid" encompasses nucleic acids with the sequence provided in or complementary to the sequence of the GenBank entry referenced in column 3 of Table 1, as well as functionally active fragments, derivatives, or orthologs thereof. A HIO nucleic acid of this disclosure may be DNA, derived from genomic DNA or cDNA, or RNA.

In one embodiment, a functionally active HIO nucleic acid encodes or is complementary to a nucleic acid that encodes a functionally active HIO polypeptide. Included within this definition is genomic DNA that serves as a template for a primary RNA transcript (i.e., an mRNA precursor) that requires processing, such as splicing, before encoding the functionally active HIO polypeptide. A HIO nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO polypeptide, or an intermediate form. A HIO polynucleotide can also include heterologous coding sequences, for example, sequences that encode a marker included to facilitate the purification of the fused polypeptide, or a transformation marker. In another embodiment, a functionally active HIO nucleic acid is capable of being used in the generation of loss-of-function HIO phenotypes, for instance, via antisense suppression, co-suppression, etc. The disclosure also provides feed, meal, grain, food, or seed comprising a nucleic acid sequence that encodes a HIO polypeptide.

In one preferred embodiment, a HIO nucleic acid used in the methods of this disclosure comprises a nucleic acid sequence that encodes or is complementary to a sequence that encodes a HIO polypeptide having at least 50%, 60%, 70%, 75%, 80%, 85%, 90%, 95%, 97%, 98% or 99% sequence identity to the disclosed HIO polypeptide sequence of the GenBank entry referenced in column 4 of Table 1 (for example the amino acid sequence set forth as SEQ ID NO: 2 or SEQ ID NO: 4).

In another embodiment a HIO polypeptide of the disclosure comprises a polypeptide sequence with at least 50% or 60% identity to the HIO polypeptide sequence as set forth as SEQ ID NO: 2 or SEQ ID NO: 4, and may have at least 70%, 80%, 85%, 90%, 95%, 97%, 98%, or 99% sequence identity to the disclosed HIO polypeptide sequence, and may include a conserved protein domain of the disclosed HIO polypeptide, such as the protein domain(s) listed in column 6 of Table 1. In another embodiment, a HIO polypeptide comprises a polypeptide sequence with at least 50%, 60%, 70%, 80%, 85%, 90%, 95%, 97%, 98%, or 99% sequence identity to a functionally active fragment of the polypeptide of the GenBank entry referenced in column 4 of Table 1, for example the amino acid sequence as set forth as SEQ ID NO: 2 or SEQ ID NO: 4. In yet another embodiment, a HIO polypeptide comprises a polypeptide sequence with at least 50%, 60%, 70%, 80%, or 90% identity to the polypeptide sequence of the GenBank entry referenced in column 4 of Table 1, for example the amino acid sequence as set forth as SEQ ID NO: 2 or SEQ ID NO: 4, over its entire length and comprises a conserved protein domain(s) listed in column 6 of Table 1.

In another aspect, a HIO polynucleotide sequence is at least 50% to 60% identical over its entire length to a disclosed HIO nucleic acid sequence, such as the nucleic acid sequence set forth as SEQ ID NO: 1 or SEQ ID NO: 3, or nucleic acid sequences that are complementary to such a HIO sequence, and may comprise at least 70%, 80%, 85%, 90% or 95% or more sequence identity over its entire length to the disclosed HIO nucleic acid sequence (for example, SEQ ID NO: 1 or SEQ ID NO: 3, or the GenBank entry referenced in column 3 of Table 1) or a functionally active fragment thereof, or nucleic acid sequences that are complementary to such a HIO sequence. In another embodiment, a disclosed HIO nucleic acid comprises a nucleic acid sequence as shown in SEQ ID NO: 1 or SEQ ID NO: 3, or nucleic acid sequences that are complementary to such a HIO sequence, and nucleic acid sequences that have substantial sequence homology to a such HIO sequences. As used herein, the phrase "substantial sequence homology" refers to those nucleic acid sequences that have slight or inconsequential sequence variations from such HIO sequences, i.e. the sequences function in substantially the same manner and encode a HIO polypeptide.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1990) 215:403-410) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. ""Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the disclosed nucleic acid sequence, for example the nucleic acid sequence as set forth as SEQ ID NO: 1 or SEQ ID NO: 3. The stringency of hybridization can be controlled by temperature, ionic strength, pH, and the presence of denaturing agents such as formamide during hybridization washing Conditions routinely used are well known (see, e.g., Current Protocol in Molecular Biology, Vol, 1, Chap, 2.10, John Wiley & Sons, Publishers (1994); Sambrook et al., Molecular Cloning, Cold Spring Harbor (1989)).

In some embodiments, a nucleic acid molecule of the disclosure is capable of hybridizing to a nucleic acid molecule, for example a nucleic acid molecule with a nucleic acid sequence as set forth as SEQ ID NO: 1 or SEQ ft NO 3, under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a HIO polypeptide can be produced. For example, codons may be selected to increase the rate at which expression of the polypeptide occurs in a particular host species, in accordance with the optimum codon usage dictated by the particular host organism (see, e.g., Nakamura et al, 1999). Such sequence variants may be used in the methods of this disclosure.

The methods of the disclosure may use orthologs of the *Arabidopsis* HIO. Putative orthologs of each of the *Arabidopsis* HIO genes identified in Table 1 below, are identified in column 8 of Table 1. Methods of identifying these and orthologs of ITO genes from other plant species are known in the art. Normally, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, *Proc Natl Acad Sci* (1998) 95:5849-5856; Huynen M A et al., *Genome Research* (2000) 10:1204-1210).

Programs for multiple sequence alignment, such as CLUSTAL (Thompson J D et al, 1994, *Nucleic Acids Res.* 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989, *Molecular Cloning: A Laboratory Manual* (Second Edition), Cold Spring Harbor Press, Plainview, N.Y.; Dieffenbach and Dveksler, 1995, *PCR Primer: A Laboratory Manual*, Cold Spring Harbor Laboratory Press, N.Y.). For instance, methods for generating a cDNA library from the plant species of interest and probing the library with partially homologous gene probes are described in Sambrook et al. A highly conserved portion of the *Arabidopsis* HIO coding sequence may be used as a probe. HIO ortholog nucleic acids may hybridize to the nucleic acid of the GenBank entry referenced in column 3 of Table 1 under high, moderate, or low stringency conditions. After amplification or isolation of a segment of a putative ortholog, that segment may be cloned and sequenced by standard techniques and utilized as a probe to isolate a complete cDNA or genomic DNA clone.

Alternatively, it is possible to initiate an EST project to generate a database of sequence information for the plant species of interest. In another approach, antibodies that specifically bind known HIO polypeptides are used for ortholog isolation (see, e.g., Harlow and Lane, 1988, 1999, *Antibodies: A Laboratory Manual*, Cold Spring Harbor Laboratory Press, N.Y.). Western blot analysis can determine that a HIO ortholog (i.e., a protein orthologous to a disclosed HIO polypeptide n) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which HIO nucleic acid and/or polypeptide sequences have been identified.

HIO nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991), may be used to introduce desired changes into a cloned nucleic acid.

In general, the methods of the disclosure involve incorporating the desired form of the HIO nucleic acid into a plant expression vector for transformation of in plant cells, and the HIO polypeptide is expressed in the host plant.

An "isolated" HIO nucleic acid molecule is other than in the form or setting in which it is found in nature and is identified and separated from least one contaminant nucleic acid molecule with which it is ordinarily associated in the natural source of the HIO nucleic acid. However, an isolated HIO nucleic acid molecule includes HIO nucleic acid molecules contained in cells that ordinarily express HIO where, for example, the nucleic acid molecule is in a chromosomal location different from that of natural cells.

TABLE 1

| 1. HIO# | 2. Tair | 3. Nucleic Acid seq. GI# | 4. Polypeptide seq. GI# | 5. Putative biochemical function/ protein name | 6. Conserved protein domain | 7. Relative Seed Oil content (%) | 8. Orthologous Genes: Nucleic Acid/Polypeptide seq. GI# Nucleic Acid GI# | Polypeptide GI# | Species |
|---|---|---|---|---|---|---|---|---|---|
| HIO30-2F (HIO30.1) | At3g54400 | gi\|30694055 SEQ ID NO: 1 | gi\|15232503 SEQ ID NO: 2 | aspartyl protease family protein | IPR001461 Peptidase A1, pepsin | 112% | gi\|30681717 SEQ ID NO: 5 | gi\|15240680 | *Arabidopsis thaliana* |
| | | | | | | | gi\|50939760 SEQ ID NO: 6 | gi\|50939761 | *Oryza sativa* (*japonica* cultivar-group) |
| | | | | | | | gi\|50904526 SEQ ID NO: 7 | gi\|50904527 | *Oryza sativa* (*japonica* cultivar-group) |
| HIO101B | At1g08520 | gi\|30680675 SEQ ID NO: 3 | gi\|30680676 SEQ ID NO: 4 | magnesium-chelatase subunit chlD, chloroplast, putative/Mg-protoporphyrin IX chelatase, putative(CHLD) | IPR000523 Magnesium chelatase, ChlI subunit | 106% | gi\|2239150 SEQ ID NO: 8 | gi\|2239151 | *Nicotiana tabacum* |
| | | | | | | | gi\|2318116 SEQ ID NO: 9 | gi\|2318117 | *Pisum sativum* |
| | | | | | | | gi\|41386844; residues 13673-2771 (reverse orientation) as contained in gi\|32982486 SEQ ID NO: 10 | gi\|50540744 | *Oryza sativa* (*japonica* cultivar-group) |

Generation of Genetically Modified Plants with an Altered Oil Content Phenotype

The disclosed HIO nucleic acids and polypeptides may be used in the generation of transgenic plants having a modified or altered oil content phenotype. As used herein, an "altered oil content (phenotype)" may refer to altered oil content in any part of the plant. In a preferred embodiment, altered expression of the HIO gene in a plant is used to generate plants with a high oil content (phenotype). The altered oil content is often observed in seeds. Examples of a transgenic plant include plants comprising a plant transformation vector with a nucleotide sequence that encodes or is complementary to a sequence that encodes a HIO polypeptide having the amino acid sequence as set forth in SEQ ID NO: 2 or SEQ ID NO: 4, or an ortholog thereof.

Any of the plants or parts thereof of the present disclosure may be processed to produce a feed, food, meal, or oil preparation. Transgenic plants, such as corn, soybean and canola containing the disclosed nucleic acid sequences, can be used in the production of vegetable oil and meal. A particularly preferred plant part for this purpose is a seed. Vegetable oil is used in a variety of food products, while meal from seed is used as an animal feed. In a preferred embodiment the feed, food, meal, or oil preparation is designed for ruminant animals. Methods to produce feed, food, meal, and oil preparations are known in the art See, for example, U.S. Pat. Nos. 4,957,748; 5,100,679; 5,219,596; 5,936,069; 6,005,076; 6,146,669; and 6,156,227. In one specific, non-limiting example of meal preparation, after harvesting seed from transgenic plants, the seed is cleaned to remove plant stalks and other material and then flaked in roller mills to break the hulls. The crushed seed is heated to 75-100° C. to denature hydrolytic enzymes, lyse the unbroken oil containing cells, and allow small oil droplets to coalesce. Most of the oil is then removed (and can be recovered) by pressing the seed material in a screw press. The remaining oil is removed from the presscake by extraction with and organic solvents, such as hexane. The solvent is removed from the meal by heating it to approximately 100° C. After drying, the meal is then granulated to a consistent form. The meal, containing the protein, digestible carbohydrate, and fiber of the seed, may be mixed with other materials prior to being used as an animal feed.

The meal of the present disclosure may be blended with other meals. In a preferred embodiment the meal produced from plants of the present disclosure or generated by a method of the present disclosure constitutes greater than about 0.5%, about 1%, about 5%, about 10%, about 25%, about 50%, about 75%, or about 90% by volume or weight of the meal component of any product. In another embodiment, the meal preparation may be blended and can constitute greater than about 10%, about 25%, about 35%, about 50%, or about 75% of the blend by volume.

The methods described herein for generating transgenic plants are generally applicable to all plants. Although activation tagging and gene identification is carried out in *Arabidopsis*, the HIO nucleic acid sequence (or an ortholog, variant or fragment thereof) may be expressed in any type of plant. In a preferred embodiment, oil-producing plants produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricin communis*), and peanut (*Arachis hypogaea*). Fruit- and vegetable-bearing plants, grain-producing plants, nut-producing plants, rapid cycling *Brassica* species, alfalfa (Medicago sativa), tobacco (Nicotiana), turfgrass (Poaceae family), other forage crops, and wild species may also be a source of unique fatty acids.

The skilled artisan will recognize that a wide variety of transformation techniques exist in the art, and new techniques are continually becoming available. Any technique that is suitable for the target host plant can be employed within the scope of the present disclosure. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, *Agrobacterium*-mediated transformation, electroporation, microinjection, microprojectile bombardment, calcium-phosphate-DNA co-precipitation, or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising a HIO polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as plants of the *Brassica* species, including canola and rapeseed, (De Block et al., 1989, *Plant Physiol*, 91:694-701), sunflower (Everett et al, 1987, *Bio/Technology*, 5:1201), and soybean (Christou et al., 1989, *Proc. Natl. Acad. Sci. USA*, 86:7500-7504; Kline et al., 1987, *Nature*, 327:70).

Expression (including transcription and translation) of a HIO nucleic acid sequence may be regulated with respect to the level of expression, the tissue type(s) where expression takes place and/or developmental stage of expression. A number of heterologous regulatory sequences (e.g., promoters and enhancers) are available for controlling the expression of an HIO nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci.* (U.S.A) 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones J D et al, 1992, *Transgenic Res.*, 1:285-297), the figwort mosaic virus 35S-promoter (U.S. Pat. No. 5,378,619), the light-inducible promoter from the small subunit of ribulose-1,5-bis-phosphate carboxylase (ss-RUBISCO), the Adh promoter (Walker et al., *Proc. Natl. Acad. Sci.* (U.S.A) 84:6624-6628, 1987), the sucrose synthase promoter (Yang et al., *Proc. Natl. Acad. Sci.* (U.S.A.) 87:4144-4148, 1990), the R gene complex promoter (Chandler et al., *The Plant Cell* 1:1175-1183, 1989), the chlorophyll a/b binding protein gene promoter, the CsVMV promoter (Verdaguer B et al., 1998, *Plant Mol. Biol.*, 37:1055-1067), the melon actin promoter (published PCT Application No. WO0056863), and the seed specific PRU promoter U.S. Patent Application Publication No. U.S. 20040064854, Clendennen et al.). Exemplary tissue-specific promoters include the tomato E4 and E8 promoters (U.S. Pat. No. 5,859,330) and the tomato 2AU gene promoter (Van Haaren M J J et al., 1993, *Plant Mol. Bio.*, 21:625-640).

In one preferred embodiment, expression of the HIO nucleic acid sequence is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., Seed Sci. Res. 1:209:219, 1991), globulin (Belanger and Kriz, Genet., 129: 863-872, 1991, GenBank Accession No. L22295), gamma zein Z 27 (Lopes et al., Mol Gen Genet., 247:603-613, 1995), L3 oleosin promoter (U.S. Pat. No. 6,433,252), phaseolin (Bustos et al., Plant Cell, 1(9):839-853, 1989), arcelin5 (U.S. Application No. 2003/0046727), a soybean 7S promoter, a 7Sα promoter (U.S. Application No. 2003/0093828), the soybean 7Sα' beta conglycinin promoter, a 7S α' promoter (Beachy et al., EMBO J, 4:3047, 1985; Schuler et al., Nucleic Acid Res., 10(24):8225-8244, 1982), soybean trypsin inhibitor (Riggs et al., Plant Cell 1(6):609-621, 1989), ACP (Baerson et al., Plant Mol. Biol., 22(2):255-267, 1993), stearoyl-ACP desaturase (Slocombe et al, Plant Physiol 104(4): 167-176, 1994), soybean a' subunit of β-conglycinin (Chen et al. Proc. Natl. Acad. Sci. 83:8560-8564, 1986), Vicia faba USP (P-Vf.Usp, SEQ ID NO: 1, 2, and 3 in (U.S. Application No. 2003/229918) and Zea mays L3 oleosin promoter (Hong et al., Plant Mol. Biol., 34(3):549-555, 1997). Also included are the zeins, which are a group of storage proteins found in corn endosperm Genomic clones for zein genes have been isolated (Pedersen et al., Cell, 29:1015-1026, 1982; and Russell et al, Transgenic Res. 6(2):157-168) and the promoters from these clones, including the 15 kD, 16 kD, 19 kD, 22 kD), 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include V. faba legumin (Baumlein et al, 1991, Mol. Gen. Genet. 225:121-8; Baumlein et al, 1992, Plant J. 2:233-9), V faba usp (Fiedler et al., 1993, Plant Mol. Biol. 22:669-79), pea convicilin (Bown et al., 1988, Biochem. J. 251:717-26), pea lectin (dePater et al., 1993, Plant Cell 5:877-86), P. vulgaris beta phaseolin (Bustos et al., 1991, EMBO J. 10:1469-79), P. vulgaris DLEC2 and PHS [beta] (Bobb et al., 1997, Nucleic Acids Res. 25:641-7), and soybean beta-Conglycinin, 7S storage protein (Chamberland et al, 1992, Plant Mol. Biol. 19:937-49).

Cereal genes whose promoters are associated with early seed and embryo development include rice glutelin ("GluA-3,"Yoshihara and Takaiwa, 1996, Plant Cell Physiol. 37:107-11; "GluB-1," Takaiwa et al., 1996, Plant Mol. Biol. 30:1207-21; Washida et al., 1999, Plant Mol. Biol. 40:1-12; "Gt3," Leisy et al., 1990, Plant Mol. Biol. 14:41-50), rice prolamin (Zhou & Fan, 1993, Transgenic Res. 2:141-6), wheat prolamin (Hammond-Kosack et al., 1993, EMBO J. 12:545-54), maize zein (Z4, Matzke et al., 1990, Plant Mol. Biol. 14:323-32), and barley B-hordeins (Entwistle et al., 1991, Plant Mol. Biol. 17:1217-31).

Other genes whose promoters are associated with early seed and embryo development include oil palm GLO7A (7S globulin, Morcillo et al., 2001, Physiol. Plant 112:233-243), Brassica napus napin, 2S storage protein, and napA gene (Josefsson et al., 1987, J. Biol. Chem. 262:12196-201; Stalberg et al., 1993, Plant Mol. Biol. 1993 23:671-83; Ellerstrom et al., 1996, Plant Mol. Biol. 32:1019-27), Brassica napus oleosin (Keddic et al., 1994, Plant Mol. Biol. 24:327-40), Arabidopsis oleosin (Plant et al., 1994, Plant Mol. Biol. 25:193-205), Arabidopsis FAE1 (Rossak et al, 2001, Plant Mol. Biol. 46:717-25), Canavalia gladiata conA (Yamamoto et al, 1995, Plant Mol. Biol. 27:729-41), and Catharanthus roseus strictosidine synthase (Str, Ouwerkerk and Memelink, 1999, Mol. Gen. Genet. 261:635-43). In another preferred embodiment, regulatory sequences from genes expressed during oil biosynthesis are used (see, e.g., U.S. Pat. No. 5,952,544). Alternative promoters are from plant storage protein genes (Bevan et al, 1993, Philos. Trans. R. Soc. Lond. B. Biol. Sci. 342:209-15). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

In yet another aspect, in some cases it may be desirable to inhibit the expression of the endogenous HIO nucleic acid sequence in a host cell. Exemplary methods for practicing this aspect of the disclosure include, but are not limited to anti-sense suppression (Smith, et al., 1988, Nature, 334:724-726; van der Krol et al., 1988, BioTechniques, 6:958-976); co-suppression (Napoli, et al., 1990, Plant Cell, 2:279-289); ribozymes (PCT Publication WO 97/10328); and combinations of sense and antisense (Waterhouse, et al., 1998, Proc. Natl. Acad. Sci. USA, 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988, Proc. Natl. Acad. Sci. USA, 85:8805-8809), a partial cDNA sequence including fragments of 5' coding sequence, (Cannon et al., 1990, Plant Mol. Biol., 15:39-47), or 3' non-coding sequences (Ch'ng et al., 1989, Proc. Natl. Acad. Sci. USA, 86:10006-10010). Cosuppression techniques may use the entire cDNA sequence (Napoli et al., 1990, Plant Cell, 2:279-289; van der Krol et al., 1990, Plant Cell, 2:291-299), or a partial cDNA sequence (Smith et al., 1990, Mol. Gen. Genetics, 224:477-481). Standard molecular and genetic tests may be performed to further analyze the association between a nucleic acid sequence and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include over-expression, ectopic expression, expression in other plant species and gene knock-out (reverse genetics, targeted knock-out, viral induced gene silencing (VIGS; see, Baulcombe D, 1999, Arch, Virol. Suppl. 15:189-201).

In a preferred application expression profiling, generally by microarray analysis, is used to simultaneously measure differences or induced changes in the expression of many different genes. Techniques for microarray analysis are well known in the art (Schena M et al., Science 1995 270:467-470; Baldwin D et al., 1999, Cur. Opin. Plant Biol. 2(2):96-103; Dangond F, Physiol Genomics (2000) 2:53-58; van Hal N L et al., J. Biotechnol. (2000) 78:271-280; Richmond T and Somerville S, Curr. Opin. Plant Biol. 2000 3:108-116). Expression profiling of individual tagged lines may be performed. Such analysis can identify other genes that are coordinately regulated as a consequence of the over-expression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Altered Oil Content Phenotype

Additional methods are disclosed herein of identifying plants that have mutations in endogenous HIO polypeptides that confer altered oil content, and generating a plant having a HIO phenotype, wherein a plant is identified that has an allele in its HIO nucleic acid sequence that results in a HIO phenotype, compared to plants lacking the allele. The plant can generate progeny, wherein the progeny inherit the allele and have a HIO phenotype. For example, provided herein is a method of identifying plants that have mutations in the endogenous HIO nucleic acid sequence that confer a HIO phenotype and generating progeny of these plants with a HIO phenotype that are not genetically modified.

In one method, called "TILLING" (for targeting induced local lesions in genomes), mutations are induced in the seed of a plant of interest, for example, using EMS (ethylmethane sulfonate) treatment. The resulting plants are grown and self-fertilized, and the progeny are used to prepare DNA samples. HIO-specific PCR is used to identify whether a mutated plant has a mutation in the HIO nucleic acid sequence. Plants having HIO mutations may then be tested for altered oil content, or alternatively, plants may be tested for altered oil content, and then PCR amplification and sequencing of the HIO nucleic acid sequence is used to determine whether a plant having altered oil content has a mutated HIO nucleic acid sequence. TILLING can identify mutations that may alter the expression of specific genes or the activity of proteins encoded by these genes (see Colbert et al., 2001, *Plant Physiol.* 126:480-484; McCallum et al., 2000, *Nature Biotechnology* 18:455-457).

In another method, a candidate gene/Quantitative Trait Locus (QTLs) approach can be used in a marker-assisted breeding program to identify alleles of or mutations in the HIO nucleic acid sequence or orthologs of the HIO nucleic acid sequence that may confer altered oil content (see Bert et al., *Theor Appl Genet.*, 2003 June; 107(1):181-9; and Lionneton et al., *Genome*, 2002 December; 45(6):1203-15). Thus, in a further aspect of the disclosure, a HIO nucleic acid is used to identify whether a plant having altered oil content has a mutation an endogenous HIO nucleic acid sequence or has a particular allele that causes altered oil content.

While the disclosure has been described with reference to specific methods and embodiments, it will be appreciated that various modifications and changes may be made without departing from the disclosure. All publications cited herein are expressly incorporated herein by reference for the purpose of describing and disclosing compositions and methodologies that might be used in connection with the disclosure.

All cited patents, patent applications, and sequence information in referenced public databases are also incorporated by reference.

EXAMPLES

Example 1

Generation of Plants with a HIO Phenotype by Transformation with an Activation Tagging Construct This Example describes the generation of transgenic plants with altered oil content.

Mutants were generated using the activation tagging "ACT-TAG" vector, pSKI015 (GI#6537289; Weigel D et al., 2000, *Plant Physiology*, 122:1003-1013). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4× CaMV 35S enhancer element. Transgenic plants were selected at the T1 generation based on herbicide resistance and T2 seed were harvested.

Quantitative determination of fatty acid content in T2 seeds was performed using the following methods for HIO30.1. A sample of 15 to 20 T2 seeds from each line tested. This sample generally contained plants with homozygous insertions, no insertions, and hemizygous insertions in a standard 1:1:2 ratios. The seed sample was massed on UMT-2 ultra-microbalance (Mettler-Toledo Co., Ohio, USA) and then transferred to a glass extraction vial. Lipids were extracted from the seeds and trans-esterified in 500 μl 2.5% $H_2SO_4$ in MeOH for 3 hours at 80° C., following the method of Browse et al (*Biochem. J.*, 235:25-31, 1986) with modifications. A known amount of heptadecanoic acid was included in the reaction as an internal standard. 750 μl of water and 400 μl of hexane were added to each vial, which was then shaken vigorously and allowed to phase separate. Reaction vials were loaded directly onto GC for analysis and the upper hexane phase was sampled by the autosampler. Gas chromatography with Flame Ionization detection was used to separate and quantify the fatty acid methyl esters, Agilent 6890 Plus GC's were used for separation with Agilent Innowax columns (30m× 0.25 mm ID, 250 μm film thickness). The carrier gas was Hydrogen at a constant flow of 2.5 ml/minute. 1 μl of sample was injected in splitless mode (inlet temperature 220° C., Purge flow 15 ml/min at 1 minute). The oven was programmed for an initial temperature of 105° C., initial time 0.5 minutes, followed by a ramp of 60° C. per minute to 175° C., a 40° C./minute ramp to 260° C. with a final hold time of 2 minutes. Detection was by Flame Ionization (Temperature 275° C., Fuel flow 30.0 ml/min, Oxidizer 400.0 ml/min). Instrument control and data collection and analysis were monitored using the Millennium Chromatography Management System (Version 3.2, Waters Corporation, Milford, Mass.). Integration and quantification were performed automatically, but all analyses were subsequently examined manually to verify correct peak identification and acceptable signal to noise ratio before inclusion of the derived results in the study.

The ACTTAG line WO00086431 was identified as having a high oil phenotype and designated as HIO30.1. Specifically, oil constituted 34.8% of seed mass (w/w) in HIO30.1 compared to an average oil content of 28.7% of other ACTTAG lines grown and analyzed in the same conditions (i.e. reference lines). Reanalysis of the same seed was performed in triplicate. Oil constituted 32.1% of seed mass, confirming an increase in oil content relative to the reference lines.

To amplify the seed stocks of the ACTTAG lines, about eighteen T2 seed were sown in soil and, after germination, exposed to the selective agent to recover transformed T2 plants. T3 seed from these plants was harvested and pooled.

T3 seed pools were analyzed for oil content by Near Infrared Spectroscopy (NIR) for HIO101B at time of harvest and for the insertion site of the ACTTAG element by inverse PCR and DNA sequencing. NIR infrared spectra were captured using a Bruker 22 N/F near infrared spectrometer Bruker Software was used to estimate total seed oil and total seed protein content using data from NIR analysis and reference methods according to the manufacturer's instructions. Oil content predicting calibrations were developed following the general method of AOCS Procedure Am1-92, Official Methods and Recommended Practices of the American Oil Chemists Society, 5th Ed., AOCS, Champaign Ill.). Calibrations allowing NIR predictions of Crude Oil (Ether Extract) (PDX-Oil3, AOAC Method 920.39 (Fat(Crude) or Ether Extract in Animal Feed, AOAC International, Official Methods of Analysis, 17th Edition, AOAC International, Gaithersburg Md.) and Crude Oil ASE (Ren Oil, Accelerated Solvent Extraction), Oil Content predicted by our calibration (PDX Oil 3, Predicts Hexane Extracted Oil) was compared for 29,746 individual T3 ACTTAG seed pools. The average NIR predicted oil content was 35.9%. Samples in the top 15% of oil content (predicted oil >=38%) were considered for further analysis. 3,870 T3 pools had high oil content by this definition. Inverse PCR was used to recover genomic DNA flanking the T-DNA insertion, which was then subjected to sequence analysis using a basic BLASTN search and/or a search of the Arabidopsis Information Resource (TAIR) database. The ACTTAG elements in approximately 40% of the lines analyzed were placed on the genome. At the time of the analysis, 478 high oil lines (as defined above) had successful placements of the ACTTAG element on the genome. Seed from both IN022173 and IN023577 had high oil (107%) and ACTTAG inserts within 10 kb of one another. The gene At1g08520 (HIO101B) lies between the insertion sites of the ACTTAG elements in these lines.

Example 2

Characterization of the T-DNA Insertion in Plants Exhibiting the Altered Oil Content (HIO) Phenotype To determine the site of the T-DNA insertion in W000086431 (HIO30.1), standard molecular analyses were performed, essentially as described in patent application PCT WO0183697. Briefly, genomic DNA was extracted from plants exhibiting the altered oil content phenotype. PCR, using primers specific to the pSKI015 vector, confirmed the presence of the 35S enhancer in plants from line W000086431, and Southern blot analysis verified the genomic integration of the ACTTAG T-DNA.

Plasmid rescue and inverse PCR were used to recover genomic DNA flanking the T-DNA insertion, which was then subjected to sequence analysis using a basic BLASTN search of the Arabidopsis Genomic DNA TAIR database (available at the publicly available Arabidopsis Information Resource website). The WO00086431 line (HIO30) has T-DNA inserted at three distinct loci.

To determine which insertion causes the high seed oil phenotype co-segregation of the high seed oil phenotype and the presence of the T-DNA was tested. Eighteen T2 plants were grown to maturity and seed harvested from these plants was used to determine that hi oil phenotype. The seed oil content from these was determined by GC analysis as described in Example 1. The genotype of the T2 seed was inferred by analyzing the T3 seed for the presence or absence of the T-DNA at the site of the insertion by PCR using primers that are specific to the corresponding genomic region and the T-DNA. The results show that the loci 2 and 3 were tightly linked. Furthermore, the average oil content of T3 seed containing the T-DNA insert at loci 2 and 3 was higher than those families lacking the insert at these loci. T2 individuals homozygous for loci 2 and 3 produced seed with an oil content of 115.4% of the reference and T2 individuals hemizygous for these loci produced seed with an oil content of 118.4% of the reference while T2 individuals lacking the T-DNA at these loci had an average oil content of 105% of a reference sample of seed from wild-type Col-O plants. Because the homozygotes and hemizygotes for the high oil loci display a similar increase in oil content, we conclude that loci 2 and 3 are linked with the high oil phenotype and the phenotype is caused by a dominant mutation. By contrast, the average oil content of T3 families containing the T-DNA insert at locus 1 was lower than or about the same as those lacking the insert at the corresponding locus. It is concluded that locus 1 is not linked to the high oil phenotype.

Sequence analysis revealed that the start codon of the nucleotide which was designated HIO30.1, was about 8 kb 5' of the downstream of the border of the T-DNA insert at locus 3.

Example 3

Analysis of Arabidopsis HIO Sequence

Sequence analyses were performed with BLAST (Altschul et al., 1990, J. Mol. Biol. 215:403-410) PFAM (Bateman et al, 1999, Nucleic Acids Res., 27:260-262), PSORT (Nakai K, and Horton P, 1999, Trends Biochem. Sci. 24:34-6), InterPro (Mulder et al., 2003, Nucleic Acids Res., 31, 315-318) and/or CLUSTAL (Thompson J D et al., 1994, Nucleic Acids Res., 22:4673-4680).

Example 4

Recapitulation of the High Oil (HIO) Phenotype

To confirm that over-expression of At3g54400 (HIO30.1) causes a high seed oil phenotype, oil content in seeds from transgenic plants over-expressing this gene was compared with oil content in seeds from non-transgenic control plants. To do this, At3g54400 was cloned into a plant transformation vector behind the seed specific PRU promoter and transformed into Arabidopsis plants using the floral dip method. The plant transformation vector contains the nptII gene, which provides resistance to kanamyacin, and serves as a selectable marker. Seed from the transformed plants were plated on agar medium containing kanamycin. After seven days, transgenic plants were identified as healthy green plants and transplanted to soil. Non-transgenic control plants were germinated on agar medium, allowed to grow for seven days and then transplanted to soil. Twenty-two transgenic seedlings and ten non-transgenic control plants were transplanted to random positions in the same 32 cell flat. The plants were grown to maturity, allowed to self-fertilize and set seed. Seed was harvested from each plant and its oil content estimated by Near Infrared (NIR) Spectroscopy using methods previously described.

The effect of over-expression of At3g54400 on seed oil has been tested in two experiments, see Table 2. In both experiments, the plants over-expressing At3g54400 had higher seed oil content than the control plants grown in the same flat. Across the experiments, the average seed oil content of plants over-expressing At3g54400 was 3% greater than the untransformed controls. The in seed oil content in plants over-expressing At3g54400 was significantly greater than non-transgenic control plants (two-way ANOVA; P=0.0477).

TABLE 2

| Experiment | Plant ID | Transgene | Predicted average | Relative value average |
|---|---|---|---|---|
| 1 | G002735001 | Pru::HIO30.1 | 33.6166 | 103.5698 |
| 1 | G002735002 | Pru::HIO30.1 | 32.4107 | 99.8547 |
| 1 | G002735003 | Pru::HIO30.1 | 32.5525 | 100.2913 |
| 1 | G002735004 | Pru::HIO30.1 | 33.0253 | 101.7482 |
| 1 | G002735005 | Pru::HIO30.1 | 34.7112 | 106.9422 |
| 1 | G002735008 | Pru::HIO30.1 | 30.3566 | 93.5262 |
| 1 | G002735010 | Pru::HIO30.1 | 33.7207 | 103.8905 |
| 1 | G002735011 | Pru::HIO30.1 | 33.7407 | 103.9523 |
| 1 | G002735012 | Pru::HIO30.1 | 35.5092 | 109.4009 |
| 1 | G002735013 | Pru::HIO30.1 | 32.5828 | 100.3848 |
| 1 | G002735014 | Pru::HIO30.1 | 30.9291 | 95.29 |
| 1 | G002735015 | Pru::HIO30.1 | 33.2569 | 102.4616 |
| 1 | G002735016 | Pru::HIO30.1 | 29.9704 | 92.3363 |
| 1 | G002735017 | Pru::HIO30.1 | 28.7109 | 88.4558 |
| 1 | G002735018 | Pru::HIO30.1 | 32.977 | 101.5994 |
| 1 | G002735019 | Pru::HIO30.1 | 32.9081 | 101.3871 |
| 1 | G002735020 | Pru::HIO30.1 | 32.0975 | 98.8895 |
| 1 | G002735021 | Pru::HIO30.1 | 32.5745 | 100.3592 |
| 1 | G002735022 | Pru::HIO30.1 | 32.4342 | 99.927 |
| 1 | G002736001 | None | 31.1896 | 96.0925 |
| 1 | G002736002 | None | 31.7842 | 97.9243 |
| 1 | G002736003 | None | 33.9313 | 104.5394 |
| 1 | G002736005 | None | 32.7659 | 100.9489 |
| 1 | G002736006 | None | 32.6891 | 100.7124 |
| 1 | G002736007 | None | 31.9202 | 98.3435 |
| 1 | G002736009 | None | 30.7591 | 94.7662 |
| 1 | G002736010 | None | 34.6237 | 106.6728 |
| 2 | DX06813001 | Pru::HIO30.1 | 26.9581 | 99.2933 |
| 2 | DX06813002 | Pru::HIO30.1 | 31.5024 | 116.0309 |
| 2 | DX06813003 | Pru::HIO30.1 | 27.7407 | 102.1759 |
| 2 | DX06813005 | Pru::HIO30.1 | 27.8096 | 102.4296 |
| 2 | DX06813006 | Pru::HIO30.1 | 27.6955 | 102.0092 |
| 2 | DX06813007 | Pru::HIO30.1 | 29.4047 | 108.3048 |
| 2 | DX06813008 | Pru::HIO30.1 | 31.3112 | 115.3268 |
| 2 | DX06813009 | Pru::HIO30.1 | 28.395 | 104.5858 |
| 2 | DX06813010 | Pru::HIO30.1 | 27.2328 | 100.305 |
| 2 | DX06813011 | Pru::HIO30.1 | 27.8172 | 102.4574 |
| 2 | DX06813012 | Pru::HIO30.1 | 31.7126 | 116.8053 |
| 2 | DX06813013 | Pru::HIO30.1 | 27.7825 | 102.3297 |
| 2 | DX06813016 | Pru::HIO30.1 | 30.1171 | 110.9288 |
| 2 | DX06813021 | Pru::HIO30.1 | 29.7314 | 109.508 |
| 2 | DX06795001 | None | 26.4647 | 97.4759 |
| 2 | DX06795002 | None | 27.6689 | 101.9113 |
| 2 | DX06795003 | None | 27.9777 | 103.0487 |
| 2 | DX06795004 | None | 28.3052 | 104.2549 |
| 2 | DX06795005 | None | 26.8591 | 98.9286 |
| 2 | DX06795006 | None | 26.8493 | 98.8927 |
| 2 | DX06795007 | None | 24.7616 | 91.2032 |
| 2 | DX06795008 | None | 26.9898 | 99.4099 |
| 2 | DX06795009 | None | 29.5455 | 108.8232 |
| 2 | DX06795010 | None | 26.078 | 96.0517 |

To confirm that over-expression of At1g08520 (HIO101B) causes a high seed oil phenotype, oil content in seeds from transgenic plants over-expressing this gene was compared with oil content in seeds from non-transgenic control plants. To do this, At1g08520 was cloned into a plant transformation vector behind the seed specific PRU promoter and transformed into *Arabidopsis* plants using the floral dip method. The plant transformation vector contains the nptII gene, which provides resistance to kanamycin, and serves as a selectable marker. Seed from the transformed plants were plated on agar medium containing kanamycin. After 7 days, transgenic plants were identified as healthy green plants and transplanted to soil. Non-transgenic control plants were germinated on agar medium, allowed to grow for 7 days and then transplanted to soil. Twenty-two transgenic seedlings and 10 non-transgenic control plants were transplanted to random positions in the same 32 cell flat. The plants were grown to maturity, allowed to self-fertilize and set seed. Seed was harvested from each plant and its oil content estimated by Near Infrared (NIR) Spectroscopy using methods previously described.

The effect of over-expression of At1g08520 on seed oil has been tested in three experiments, see Table 3. In all three experiments, the plants over-expressing At1g08520 had higher seed oil content than the control plants grown in the same flat. Across the experiments, the average seed oil content of plants over-expressing At1g08520 was 5% greater than the untransformed controls. The in seed oil content in plants over-expressing At1g08520 was significantly greater than non-transgenic control plants (two-way ANOVA; P=0.0030).

TABLE 3

| Experiment | Plant ID | Transgene | Predicted Oil | Relative Oil value |
|---|---|---|---|---|
| 1 | Z003907002 | Pru::HIO101B | 34.5351 | 109.0118 |
| 1 | Z003907003 | Pru::HIO101B | 35.7637 | 112.8898 |
| 1 | Z003907004 | Pru::HIO101B | 36.1101 | 113.9832 |
| 1 | Z003907005 | Pru::HIO101B | 35.0344 | 110.5877 |
| 1 | Z003907006 | Pru::HIO101B | 33.6465 | 106.2067 |
| 1 | Z003907008 | Pru::HIO101B | 31.572 | 99.6584 |
| 1 | Z003907009 | Pru::HIO101B | 34.8969 | 110.1536 |
| 1 | Z003907011 | Pru::HIO101B | 33.2621 | 104.9933 |
| 1 | Z003907012 | Pru::HIO101B | 33.7056 | 106.3933 |
| 1 | Z003907013 | Pru::HIO101B | 34.043 | 107.4582 |
| 1 | Z003907017 | Pru::HIO101B | 30.5754 | 96.5128 |
| 1 | Z003907019 | Pru::HIO101B | 30.5735 | 96.5067 |
| 1 | Z003907021 | Pru::HIO101B | 35.6997 | 112.6879 |
| 1 | Z003910001 | None | 32.4184 | 102.3301 |
| 1 | Z003910002 | None | 31.8453 | 100.5212 |
| 1 | Z003910003 | None | 33.7541 | 106.5466 |
| 1 | Z003910004 | None | 32.409 | 102.3006 |
| 1 | Z003910005 | None | 31.2691 | 98.7024 |
| 1 | Z003910006 | None | 30.9758 | 97.7767 |
| 1 | Z003910007 | None | 30.6926 | 96.8827 |
| 1 | Z003910008 | None | 31.7123 | 100.1015 |
| 1 | Z003910009 | None | 30.4135 | 96.0018 |
| 1 | Z003910010 | None | 31.3115 | 98.8364 |
| 2 | Z003985002 | Pru::HIO101B | 29.2672 | 94.4525 |
| 2 | Z003985003 | Pru::HIO101B | 34.2542 | 110.5467 |
| 2 | Z003985006 | Pru::HIO101B | 34.5119 | 111.3785 |
| 2 | Z003985008 | Pru::HIO101B | 33.6445 | 108.579 |
| 2 | Z003985010 | Pru::HIO101B | 29.9842 | 96.7665 |
| 2 | Z003985011 | Pru::HIO101B | 31.1537 | 100.5408 |
| 2 | Z003985013 | Pru::HIO101B | 36.1835 | 116.7732 |
| 2 | Z003985018 | Pru::HIO101B | 35.0497 | 113.1142 |
| 2 | Z003985019 | Pru::HIO101B | 35.7475 | 115.3661 |
| 2 | Z004001001 | None | 34.5363 | 111.4571 |
| 2 | Z004001002 | None | 31.3602 | 101.207 |
| 2 | Z004001003 | None | 25.9146 | 83.6327 |
| 2 | Z004001004 | None | 28.7292 | 92.7163 |
| 2 | Z004001005 | None | 27.8834 | 89.9866 |
| 2 | Z004001006 | None | 30.4942 | 98.4123 |
| 2 | Z004001007 | None | 31.7341 | 102.4136 |
| 2 | Z004001008 | None | 27.5432 | 88.8887 |
| 2 | Z004001009 | None | 35.3457 | 114.0693 |
| 2 | Z004001010 | None | 36.3209 | 117.2164 |
| 3 | DX06630001 | Pru::HIO101B | 29.8335 | 97.0689 |

TABLE 3-continued

| Experiment | Plant ID | Transgene | Predicted Oil | Relative Oil value |
|---|---|---|---|---|
| 3 | DX06630002 | Pru::HIO101B | 29.1628 | 94.8866 |
| 3 | DX06630003 | Pru::HIO101B | 29.5618 | 96.185 |
| 3 | DX06630004 | Pru::HIO101B | 34.1125 | 110.9915 |
| 3 | DX06630005 | Pru::HIO101B | 29.9095 | 97.3163 |
| 3 | DX06630009 | Pru::HIO101B | 31.2482 | 101.6719 |
| 3 | DX06630010 | Pru::HIO101B | 31.3747 | 102.0834 |
| 3 | DX06630011 | Pru::HIO101B | 29.3162 | 95.3858 |
| 3 | DX06630012 | Pru::HIO101B | 33.8001 | 109.975 |
| 3 | DX06630013 | Pru::HIO101B | 32.1773 | 104.6949 |
| 3 | DX06630014 | Pru::HIO101B | 33.8088 | 110.0032 |
| 3 | DX06630015 | Pru::HIO101B | 30.963 | 100.7439 |
| 3 | DX06612001 | None | 30.3733 | 98.8253 |
| 3 | DX06612002 | None | 30.1554 | 98.1162 |
| 3 | DX06612003 | None | 30.7265 | 99.9744 |
| 3 | DX06612004 | None | 31.8674 | 103.6867 |
| 3 | DX06612005 | None | 30.4838 | 99.1849 |
| 3 | DX06612006 | None | 29.9795 | 97.5438 |
| 3 | DX06612007 | None | 30.9704 | 100.7679 |
| 3 | DX06612008 | None | 31.4789 | 102.4224 |
| 3 | DX06612009 | None | 31.0681 | 101.0858 |
| 3 | DX06612010 | None | 30.2404 | 98.3927 |

Example 5

To confirm that the high seed oil phenotype in plants overexpressing HIO30.1 is heritable, seed oil content from the progeny of a transgenic line displaying a high oil phenotype (DX06813012) was compared with oil content in seeds from non-transgenic control plants. To do this, T2 seed from DX06813012 was plated on agar medium containing kanamycin to identify plants containing the transgene. After seven days, transgenic plants were identified as healthy green plants and transplanted to soil. Non-transgenic control plants were germinated on agar medium, allowed to grow for seven days and then transplanted to soil. Twenty-two transgenic seedlings and ten non-transgenic control plants were transplanted to random positions in the same 32 cell flat. The plants were grown to maturity, allowed to self-fertilize and set seed. Seed was harvested from each plant and its oil content estimated by Near Infrared (NIR) Spectroscopy using methods previously described.

The seed oil content in the progeny of DX06813012 was higher than the seed oil content of control plants grown in the same tray, see Table 4. The average seed oil content of the progeny of DX06813012 was 4.6% greater than the untransformed controls. This increase was determined to be significant by a T-test (P value=0.0015).

TABLE 4

| Exp. No. | Plant ID | Seed Generation | Parent | Transgene | Predicted Average | Relative Value Average |
|---|---|---|---|---|---|---|
| 1 | DX08262001 | T3 | DX06813012 | Pru::HIO30.1 | 35.32 | 105.46 |
| 1 | DX08262002 | T3 | DX06813012 | Pru::HIO30.1 | 34.89 | 104.18 |
| 1 | DX08262003 | T3 | DX06813012 | Pru::HIO30.1 | 32.89 | 98.22 |
| 1 | DX08262004 | T3 | DX06813012 | Pru::HIO30.1 | 34.31 | 102.47 |
| 1 | DX08262005 | T3 | DX06813012 | Pru::HIO30.1 | 33.8 | 100.93 |
| 1 | DX08262006 | T3 | DX06813012 | Pru::HIO30.1 | 36.18 | 108.04 |
| 1 | DX08262007 | T3 | DX06813012 | Pru::HIO30.1 | 33.26 | 99.32 |
| 1 | DX08262008 | T3 | DX06813012 | Pru::HIO30.1 | 32.13 | 95.94 |
| 1 | DX08262009 | T3 | DX06813012 | Pru::HIO30.1 | 34.82 | 103.98 |
| 1 | DX08262010 | T3 | DX06813012 | Pru::HIO30.1 | 35.42 | 105.77 |
| 1 | DX08262011 | T3 | DX06813012 | Pru::HIO30.1 | 33.97 | 101.44 |
| 1 | DX08262012 | T3 | DX06813012 | Pru::HIO30.1 | 34.34 | 102.56 |
| 1 | DX08262013 | T3 | DX06813012 | Pru::HIO30.1 | 36.79 | 109.85 |
| 1 | DX08262014 | T3 | DX06813012 | Pru::HIO30.1 | 33.43 | 99.83 |
| 1 | DX08262015 | T3 | DX06813012 | Pru::HIO30.1 | 35.89 | 107.18 |
| 1 | DX08262016 | T3 | DX06813012 | Pru::HIO30.1 | 33.79 | 100.9 |
| 1 | DX08262017 | T3 | DX06813012 | Pru::HIO30.1 | 36.4 | 108.69 |
| 1 | DX08262018 | T3 | DX06813012 | Pru::HIO30.1 | 37.13 | 110.88 |
| 1 | DX08262019 | T3 | DX06813012 | Pru::HIO30.1 | 34.5 | 103.01 |
| 1 | DX08262020 | T3 | DX06813012 | Pru::HIO30.1 | 35.8 | 106.92 |
| 1 | DX08262021 | T3 | DX06813012 | Pru::HIO30.1 | 37.71 | 112.62 |
| 1 | DX08262022 | T3 | DX06813012 | Pru::HIO30.1 | 37.92 | 113.23 |
| 1 | DX08278001 | T3 | COL-0 | None | 34.14 | 101.94 |
| 1 | DX08278002 | T3 | COL-0 | None | 33.98 | 101.47 |
| 1 | DX08278003 | T3 | COL-0 | None | 31.94 | 95.39 |
| 1 | DX08278004 | T3 | COL-0 | None | 33.86 | 101.1 |
| 1 | DX08278005 | T3 | COL-0 | None | 32.46 | 96.93 |
| 1 | DX08278006 | T3 | COL-0 | None | 32.91 | 98.27 |
| 1 | DX08278007 | T3 | COL-0 | None | 33.53 | 100.14 |
| 1 | DX08278008 | T3 | COL-0 | None | 33.69 | 100.62 |
| 1 | DX08278009 | T3 | COL-0 | None | 33.26 | 99.32 |
| 1 | DX08278010 | T3 | COL-0 | None | 35.1 | 104.82 |

To confirm that the high seed oil phenotype in plants overexpressing HIO101B is heritable, seed oil content from the progeny of 4 transgenic lines displaying high oil phenotypes (Z003907005, Z003907008, Z003907013 and Z003907018) was compared with oil content in seeds from non-transgenic control plants. To do this, T2 seed from Z003907005, Z003907008, Z003907013 and Z003907018 were plated on agar medium containing kanamycin to identify plants containing the transgene. After seven days, transgenic plants were identified as healthy green plants and transplanted to soil. Non-transgenic control plants were germinated on agar medium, allowed to grow for seven days and then transplanted to soil. Twenty-two transgenic seedlings from each line and ten non-transgenic control plants were transplanted to random positions in four 32 cell flats. The plants were grown to maturity, allowed to self-fertilize and set seed. Seed was harvested from each plant and its oil content estimated by Near Infrared (NIR) Spectroscopy using methods previously described.

The seed oil content in the progeny of the transgenic lines was higher than the seed oil content of control plants grown in the same tray, see Table 5. The average seed oil content of the progeny of Z003907005, Z003907008, Z003907013 and Z003907018 were 6.3, 10.1, 3.0 and 3.3% greater than the untransformed controls grown in the same tray, respectively. These increases were determined to be significant by a T-test (P values=0.0015, 0.003, 0.026 and 0.013, respectively).

TABLE 5

| Exp. No. | Plant | Seed Generation | Parent | Transgene | Predicted Average | Relative Value Average |
|---|---|---|---|---|---|---|
| 1 | DX06905001 | T3 | Z003907005 | Pru::HIO101B | 34.34 | 114.9 |
| 1 | DX06905002 | T3 | Z003907005 | Pru::HIO101B | 34.42 | 115.2 |
| 1 | DX06905003 | T3 | Z003907005 | Pru::HIO101B | 32.17 | 107.7 |
| 1 | DX06905004 | T3 | Z003907005 | Pru::HIO101B | 32.2 | 107.8 |
| 1 | DX06905005 | T3 | Z003907005 | Pru::HIO101B | 34.04 | 113.9 |
| 1 | DX06905006 | T3 | Z003907005 | Pru::HIO101B | 31.8 | 106.5 |
| 1 | DX06905007 | T3 | Z003907005 | Pru::HIO101B | 32.13 | 107.6 |
| 1 | DX06905008 | T3 | Z003907005 | Pru::HIO101B | 33.73 | 112.9 |
| 1 | DX06905009 | T3 | Z003907005 | Pru::HIO101B | 31.78 | 106.4 |
| 1 | DX06905010 | T3 | Z003907005 | Pru::HIO101B | 33.19 | 111.1 |
| 1 | DX06905011 | T3 | Z003907005 | Pru::HIO101B | 29.43 | 98.5 |
| 1 | DX06905012 | T3 | Z003907005 | Pru::HIO101B | 33.73 | 112.9 |
| 1 | DX06905013 | T3 | Z003907005 | Pru::HIO101B | 30.89 | 103.4 |
| 1 | DX06905014 | T3 | Z003907005 | Pru::HIO101B | 25.1 | 84.0 |
| 1 | DX06905015 | T3 | Z003907005 | Pru::HIO101B | 29.56 | 99.0 |
| 1 | DX06905016 | T3 | Z003907005 | Pru::HIO101B | 29.69 | 99.4 |
| 1 | DX06905017 | T3 | Z003907005 | Pru::HIO101B | 31.21 | 104.5 |
| 1 | DX06905018 | T3 | Z003907005 | Pru::HIO101B | 32.73 | 109.6 |
| 1 | DX06905019 | T3 | Z003907005 | Pru::HIO101B | 30.23 | 101.2 |
| 1 | DX06905020 | T3 | Z003907005 | Pru::HIO101B | 32.88 | 110.1 |
| 1 | DX06905021 | T3 | Z003907005 | Pru::HIO101B | 32.27 | 108.0 |
| 1 | DX06905022 | T3 | Z003907005 | Pru::HIO101B | 30.9 | 103.4 |
| 1 | DX06919001 | T3 | COL-0 | None | 29.03 | 97.2 |
| 1 | DX06919002 | T3 | COL-0 | None | 30.87 | 103.3 |
| 1 | DX06919003 | T3 | COL-0 | None | 32.64 | 109.3 |
| 1 | DX06919004 | T3 | COL-0 | None | 31.55 | 105.6 |
| 1 | DX06919005 | T3 | COL-0 | None | 31.18 | 104.4 |
| 1 | DX06919006 | T3 | COL-0 | None | 28.45 | 95.2 |
| 1 | DX06919007 | T3 | COL-0 | None | 28.96 | 97.0 |
| 1 | DX06919008 | T3 | COL-0 | None | 28.62 | 95.8 |
| 1 | DX06919009 | T3 | COL-0 | None | 30.38 | 101.7 |
| 1 | DX06919010 | T3 | COL-0 | None | 27.04 | 90.5 |
| 2 | DX07000001 | T3 | Z003907008 | Pru::HIO101B | 30.72 | 103.6 |
| 2 | DX07000003 | T3 | Z003907008 | Pru::HIO101B | 30.12 | 101.6 |
| 2 | DX07000004 | T3 | Z003907008 | Pru::HIO101B | 32.09 | 108.3 |
| 2 | DX07000005 | T3 | Z003907008 | Pru::HIO101B | 34.17 | 115.3 |
| 2 | DX07000007 | T3 | Z003907008 | Pru::HIO101B | 33.99 | 114.6 |
| 2 | DX07000008 | T3 | Z003907008 | Pru::HIO101B | 33.14 | 111.8 |
| 2 | DX07000009 | T3 | Z003907008 | Pru::HIO101B | 32.91 | 111.0 |
| 2 | DX07000010 | T3 | Z003907008 | Pru::HIO101B | 33.94 | 114.5 |
| 2 | DX07008001 | T3 | COL-0 | None | 30.17 | 101.8 |
| 2 | DX07008002 | T3 | COL-0 | None | 27.75 | 93.6 |
| 2 | DX07008003 | T3 | COL-0 | None | 27.48 | 92.7 |
| 2 | DX07008004 | T3 | COL-0 | None | 32.74 | 110.4 |
| 2 | DX07008005 | T3 | COL-0 | None | 29.53 | 99.6 |
| 2 | DX07008006 | T3 | COL-0 | None | 27.46 | 92.6 |
| 2 | DX07008007 | T3 | COL-0 | None | 32.13 | 108.4 |
| 2 | DX07008008 | T3 | COL-0 | None | 30.97 | 104.5 |
| 2 | DX07008010 | T3 | COL-0 | None | 28.55 | 96.3 |
| 3 | DX06908001 | T3 | Z003907013 | Pru::HIO101B | 32.84 | 105.0 |
| 3 | DX06908002 | T3 | Z003907013 | Pru::HIO101B | 33.59 | 107.4 |
| 3 | DX06908003 | T3 | Z003907013 | Pru::HIO101B | 33.03 | 105.7 |
| 3 | DX06908004 | T3 | Z003907013 | Pru::HIO101B | 32.38 | 103.6 |
| 3 | DX06908005 | T3 | Z003907013 | Pru::HIO101B | 32.79 | 104.9 |
| 3 | DX06908006 | T3 | Z003907013 | Pru::HIO101B | 32.36 | 103.5 |
| 3 | DX06908007 | T3 | Z003907013 | Pru::HIO101B | 34.42 | 110.1 |

TABLE 5-continued

| Exp. No. | Plant | Seed Generation | Parent | Transgene | Predicted Average | Relative Value Average |
|---|---|---|---|---|---|---|
| 3 | DX06908008 | T3 | Z003907013 | Pru::HIO101B | 34.02 | 108.8 |
| 3 | DX06908009 | T3 | Z003907013 | Pru::HIO101B | 31.19 | 99.8 |
| 3 | DX06908010 | T3 | Z003907013 | Pru::HIO101B | 29.75 | 95.2 |
| 3 | DX06908011 | T3 | Z003907013 | Pru::HIO101B | 32.78 | 104.9 |
| 3 | DX06908012 | T3 | Z003907013 | Pru::HIO101B | 32.25 | 103.2 |
| 3 | DX06908013 | T3 | Z003907013 | Pru::HIO101B | 32.1 | 102.7 |
| 3 | DX06908014 | T3 | Z003907013 | Pru::HIO101B | 31.23 | 99.9 |
| 3 | DX06908015 | T3 | Z003907013 | Pru::HIO101B | 32.26 | 103.2 |
| 3 | DX06908016 | T3 | Z003907013 | Pru::HIO101B | 32.25 | 103.2 |
| 3 | DX06908017 | T3 | Z003907013 | Pru::HIO101B | 32.13 | 102.8 |
| 3 | DX06908018 | T3 | Z003907013 | Pru::HIO101B | 32.1 | 102.7 |
| 3 | DX06908019 | T3 | Z003907013 | Pru::HIO101B | 31.15 | 99.6 |
| 3 | DX06908020 | T3 | Z003907013 | Pru::HIO101B | 30.27 | 96.8 |
| 3 | DX06908021 | T3 | Z003907013 | Pru::HIO101B | 32.89 | 105.2 |
| 3 | DX06908022 | T3 | Z003907013 | Pru::HIO101B | 30.98 | 99.1 |
| 3 | DX06922001 | T3 | COL-0 | None | 30.65 | 98.0 |
| 3 | DX06922002 | T3 | COL-0 | None | 32.52 | 104.0 |
| 3 | DX06922004 | T3 | COL-0 | None | 32.1 | 102.7 |
| 3 | DX06922005 | T3 | COL-0 | None | 29.57 | 94.6 |
| 3 | DX06922006 | T3 | COL-0 | None | 31.56 | 101.0 |
| 3 | DX06922007 | T3 | COL-0 | None | 31.24 | 99.9 |
| 3 | DX06922008 | T3 | COL-0 | None | 31.85 | 101.9 |
| 3 | DX06922009 | T3 | COL-0 | None | 30.34 | 97.0 |
| 3 | DX06922010 | T3 | COL-0 | None | 31.54 | 100.9 |
| 4 | DX06911001 | T3 | Z003985018 | Pru::HIO101B | 28.83 | 102.3 |
| 4 | DX06911003 | T3 | Z003985018 | Pru::HIO101B | 27.82 | 98.7 |
| 4 | DX06911004 | T3 | Z003985018 | Pru::HIO101B | 27.08 | 96.1 |
| 4 | DX06911005 | T3 | Z003985018 | Pru::HIO101B | 28.37 | 100.6 |
| 4 | DX06911006 | T3 | Z003985018 | Pru::HIO101B | 28.65 | 101.6 |
| 4 | DX06911007 | T3 | Z003985018 | Pru::HIO101B | 29.94 | 106.2 |
| 4 | DX06911008 | T3 | Z003985018 | Pru::HIO101B | 30.08 | 106.7 |
| 4 | DX06911009 | T3 | Z003985018 | Pru::HIO101B | 28.09 | 99.6 |
| 4 | DX06911010 | T3 | Z003985018 | Pru::HIO101B | 28.84 | 102.3 |
| 4 | DX06911011 | T3 | Z003985018 | Pru::HIO101B | 28.68 | 101.7 |
| 4 | DX06911012 | T3 | Z003985018 | Pru::HIO101B | 28.1 | 99.7 |
| 4 | DX06911013 | T3 | Z003985018 | Pru::HIO101B | 31.92 | 113.2 |
| 4 | DX06911014 | T3 | Z003985018 | Pru::HIO101B | 31.01 | 110.0 |
| 4 | DX06911015 | T3 | Z003985018 | Pru::HIO101B | 29.71 | 105.4 |
| 4 | DX06911016 | T3 | Z003985018 | Pru::HIO101B | 27.73 | 98.4 |
| 4 | DX06911017 | T3 | Z003985018 | Pru::HIO101B | 28.75 | 102.0 |
| 4 | DX06911018 | T3 | Z003985018 | Pru::HIO101B | 29.01 | 102.9 |
| 4 | DX06911019 | T3 | Z003985018 | Pru::HIO101B | 31.19 | 110.6 |
| 4 | DX06911020 | T3 | Z003985018 | Pru::HIO101B | 28.7 | 101.8 |
| 4 | DX06911021 | T3 | Z003985018 | Pru::HIO101B | 29.4 | 104.3 |
| 4 | DX06911022 | T3 | Z003985018 | Pru::HIO101B | 29.96 | 106.3 |
| 4 | DX06925001 | T3 | COL-0 | None | 27.25 | 96.7 |
| 4 | DX06925002 | T3 | COL-0 | None | 28.38 | 100.7 |
| 4 | DX06925003 | T3 | COL-0 | None | 29 | 102.9 |
| 4 | DX06925004 | T3 | COL-0 | None | 27.52 | 97.6 |
| 4 | DX06925005 | T3 | COL-0 | None | 27.07 | 96.0 |
| 4 | DX06925006 | T3 | COL-0 | None | 29.36 | 104.1 |
| 4 | DX06925007 | T3 | COL-0 | None | 27.98 | 99.2 |
| 4 | DX06925008 | T3 | COL-0 | None | 28.83 | 102.3 |
| 4 | DX06925009 | T3 | COL-0 | None | 28.24 | 100.2 |
| 4 | DX06925010 | T3 | COL-0 | None | 28.31 | 100.4 |

This disclosure describes the discovery of plants and plant cells that display an altered oil content phenotype due to altered expression of a HIO nucleic acid, and related methods and compositions useful for exploiting this discovery. It will be apparent that the precise details of the methods described may be varied or modified without departing from the spirit of the described invention. We claim all such modifications and variations that fall within the scope and spirit of the disclosure and the claims below.

It is claimed:

1. A method of producing a high oil phenotype in a plant, said method comprising:
  a) introducing into progenitor cells of the plant a plant transformation vector comprising a heterologous constitutive promoter operatively linked to a nucleotide sequence that encodes a polypeptide comprising an amino acid sequence having at least 95% sequence identity to the amino acid sequence of SEQ ID NO: 2 to produce transformed progenitor cells overexpressing the polypeptide;
  b) growing the transformed progenitor cells to produce a transgenic plant overexpressing said polypeptide; and
  c) identifying a high oil phenotype in said transgenic plant relative to a plant of the same species that does not comprise the plant transformation vector, thereby producing the high oil phenotype in said transgenic plant.

2. The method of claim 1, wherein the nucleotide sequence encodes a polypeptide consisting of an amino acid sequence having at least 95% sequence identity to the amino acid sequence of SEQ ID NO: 2.

3. The method of claim 1, wherein the nucleotide sequence encodes a polypeptide comprising the amino acid sequence set forth as SEQ ID NO: 2.

4. The method of claim 1, wherein the nucleotide sequence encodes a polypeptide consisting of the amino acid sequence set forth as SEQ ID NO: 2.

5. A method of producing oil comprising:
  growing a transgenic plant comprising a plant transformation vector comprising a nucleotide sequence that encodes a polypeptide comprising an amino acid sequence having at least 95% sequence identity to the amino acid sequence of SEQ ID NO: 2, whereby overexpression of the polypeptide in the transgenic plant results in a high oil phenotype relative to a plant of the same species that does not comprise the plant transformation vector; and recovering the oil from said transgenic plant.

6. The method of claim 5, wherein the oil is recovered from a seed of the plant, wherein said seed comprises the plant transformation vector.

7. The method of claim 5, wherein the nucleotide sequence encodes a polypeptide consisting of an amino acid sequence having at least 95% sequence identity to the amino acid sequence of SEQ ID NO: 2.

8. The method of claim 5, wherein the nucleotide sequence encodes a polypeptide comprising the amino acid sequence set forth as SEQ ID NO: 2.

9. The method of claim 5, wherein the nucleotide sequence encodes a polypeptide consisting of the amino acid sequence set forth as SEQ ID NO: 2.

* * * * *

UNITED STATES PATENT AND TRADEMARK OFFICE
CERTIFICATE OF CORRECTION

| | |
|---|---|
| PATENT NO. | : 7,663,020 B2 |
| APPLICATION NO. | : 11/813858 |
| DATED | : February 16, 2010 |
| INVENTOR(S) | : Davies and Ng |

Page 1 of 1

It is certified that error appears in the above-identified patent and that said Letters Patent is hereby corrected as shown below:

Column 3, line 50, "plant In" should read --plant. In--.

Column 5, line 59, "id-type" should read --wild-type--.

Column 10, line 6, "modified" should read --modified.--.

Column 18, line 66, "2AU" should read --2AII--.

Column 19, line 27, "endosperm Genomic" should read --endosperm. Genomic--.

Column 19, line 30, "22 kD)," should read --22 kD,--.

Column 24, line 5, "hi oil" should read --high oil--.

Column 24, line 25, "T3families" should read --T3 families--.

Signed and Sealed this

Ninth Day of November, 2010

David J. Kappos
*Director of the United States Patent and Trademark Office*

SEQUENCE LISTING

<160> NUMBER OF SEQ ID NOS: 10

<210> SEQ ID NO 1

<211> LENGTH: 1554
<212> TYPE: DNA
<213> ORGANISM: Arabidopsis thaliana

<400> SEQUENCE: 1

```
acaaacacta gaaaccacaa agacaaaatc aaggtcttaa acaatgagat cccatctctt     60
gattttgtta atctctctct taatcttgaa atctgaatcc ataaactgca atgaaaagag    120
ccattcctca gatctaagag tgttccacat taacagtcta tgttctccat tcaaaacttc    180
tgtttcatgg gcagatacac ttcttcaaga taaggctcgt ttcctatact tgtcaagcct    240
cgctggcgtt aggaaatcat cagttccaat cgcctctggt cgggccatcg ttcagagccc    300
gacttacatc gtgagggcta acatcgggac accggctcag cccatgctcg tggctcttga    360
cactagcaat gacgctgctt ggattccttg ttctggctgc gttggctgtt cttcctctgt    420
tctctttgac ccttccaagt caagctcctc tcgtactctt caatgcgaag ctcctcagtg    480
taaacaggct ccaaatccaa gttgcacagt aagcaaatca tgtggtttca acatgaccta    540
cggtggttca accatcgaag catatctgac acaagacaca ctaacattgg ccagtgacgt    600
catcccaaac tacaccttg ggtgcatcaa caaagctagt ggaacatcgt tgccagcgca    660
aggactcatg ggcttaggtc gtggtccatt gtctttaatc tcacagtcac aaaatcttta    720
tcagtctaca tttctcgtatt gcttgcctaa tagtaagtcc agcaatttct ccggatcact    780
aagattggga cctaagaacc aaccgatccg gatcaagacc actccattgt taaagaaccc    840
tagaagatca tcgctttact atgttaactt ggttgggatt cgtgtcggaa acaaaattgt    900
ggatattcct acaagtgcac tcgcctttga tccggccacc ggagccggca ccatctttga    960
ctcggggacg gtctacacaa ggctagtcga accagcttac gtggcggtga gaaacgagtt   1020
caggagacgt gttaagaacg caaacgcaac ttcactagga ggtttcgaca catgctactc   1080
cggctccgtc gtgttcccgt cggtgacgtt tatgttcgcc ggaatgaacg tgactctgcc   1140
tccagacaac cttctcatcc acagctccgc aggtaacctc agctgcctcg ccatggctgc   1200
agctccggtc aacgttaact ctgtccttaa cgtcatcgct agtatgcagc aacagaacca   1260
ccgagttctc atcgacgttc caaattccag gctcggaatt tcccgtgaaa cttgcaccta   1320
agttttatcg atttgtattt ttgttttcgg tcgatttcgt aatgcgtttt gaacttttga   1380
attttggaaa ctatataagt taatgatttt tgttaattct caaacgattg taaaatcttt   1440
cgtatgattt tctttcgatg ttctctgttc aaaaaggatt gtactcatga atttgcggat   1500
gcaataagcc tggaacagag gacctttatt attttaaata tatatatgtt ccaa         1554
```

<210> SEQ ID NO 2
<211> LENGTH: 425
<212> TYPE: PRT
<213> ORGANISM: Arabidopsis thaliana

<400> SEQUENCE: 2

```
Met Arg Ser His Leu Leu Ile Leu Leu Ile Ser Leu Leu Ile Leu Lys
1               5                   10                  15

Ser Glu Ser Ile Asn Cys Asn Glu Lys Ser His Ser Ser Asp Leu Arg
            20                  25                  30

Val Phe His Ile Asn Ser Leu Cys Ser Pro Phe Lys Thr Ser Val Ser
        35                  40                  45

Trp Ala Asp Thr Leu Leu Gln Asp Lys Ala Arg Phe Leu Tyr Leu Ser
    50                  55                  60

Ser Leu Ala Gly Val Arg Lys Ser Ser Val Pro Ile Ala Ser Gly Arg
```

-continued

```
                65                  70                  75                  80
Ala Ile Val Gln Ser Pro Thr Tyr Ile Val Arg Ala Asn Ile Gly Thr
                    85                  90                  95

Pro Ala Gln Pro Met Leu Val Ala Leu Asp Thr Ser Asn Asp Ala Ala
                100                 105                 110

Trp Ile Pro Cys Ser Gly Cys Val Gly Cys Ser Ser Val Leu Phe
            115                 120                 125

Asp Pro Ser Lys Ser Ser Ser Arg Thr Leu Gln Cys Glu Ala Pro
        130                 135                 140

Gln Cys Lys Gln Ala Pro Asn Pro Ser Cys Thr Val Ser Lys Ser Cys
145                 150                 155                 160

Gly Phe Asn Met Thr Tyr Gly Gly Ser Thr Ile Glu Ala Tyr Leu Thr
                165                 170                 175

Gln Asp Thr Leu Thr Leu Ala Ser Asp Val Ile Pro Asn Tyr Thr Phe
                180                 185                 190

Gly Cys Ile Asn Lys Ala Ser Gly Thr Ser Leu Pro Ala Gln Gly Leu
            195                 200                 205

Met Gly Leu Gly Arg Gly Pro Leu Ser Leu Ile Ser Gln Ser Gln Asn
        210                 215                 220

Leu Tyr Gln Ser Thr Phe Ser Tyr Cys Leu Pro Asn Ser Lys Ser Ser
225                 230                 235                 240

Asn Phe Ser Gly Ser Leu Arg Leu Gly Pro Lys Asn Gln Pro Ile Arg
                245                 250                 255

Ile Lys Thr Thr Pro Leu Leu Lys Asn Pro Arg Arg Ser Ser Leu Tyr
                260                 265                 270

Tyr Val Asn Leu Val Gly Ile Arg Val Gly Asn Lys Ile Val Asp Ile
            275                 280                 285

Pro Thr Ser Ala Leu Ala Phe Asp Pro Ala Thr Gly Ala Gly Thr Ile
        290                 295                 300

Phe Asp Ser Gly Thr Val Tyr Thr Arg Leu Val Glu Pro Ala Tyr Val
305                 310                 315                 320

Ala Val Arg Asn Glu Phe Arg Arg Val Lys Asn Ala Asn Ala Thr
                325                 330                 335

Ser Leu Gly Gly Phe Asp Thr Cys Tyr Ser Gly Ser Val Val Phe Pro
            340                 345                 350

Ser Val Thr Phe Met Phe Ala Gly Met Asn Val Thr Leu Pro Pro Asp
        355                 360                 365

Asn Leu Leu Ile His Ser Ala Gly Asn Leu Ser Cys Leu Ala Met
        370                 375                 380

Ala Ala Ala Pro Val Asn Val Asn Ser Val Leu Asn Val Ile Ala Ser
385                 390                 395                 400

Met Gln Gln Gln Asn His Arg Val Leu Ile Asp Val Pro Asn Ser Arg
                405                 410                 415

Leu Gly Ile Ser Arg Glu Thr Cys Thr
            420                 425

<210> SEQ ID NO 3
<211> LENGTH: 2548
<212> TYPE: DNA
<213> ORGANISM: Arabidopsis thaliana

<400> SEQUENCE: 3
gcaatcagga aaggatgacg agacaaaaga tagagaagca aaagtaagct gataaggttt      60
gatacagtag aaaatactat ctcttaactt cttcttcttc ttcttcttct tctcctatct     120
```

-continued

```
ttgaaaatgg cgatgactcc ggtcgcgtca tcatctccag tttcaacctg cagactcttt    180
cgctgcaatc tcctccctga tctcttacct aagcctctgt ttctctccct ccccaaacga    240
aacagaattg cctcgtgccg cttcactgta cgtgcctccg cgaatgctac cgtcgaatcc    300
cctaacggtg tccctgcctc cacatcagat acggatacgg agacggatac cacctcctat    360
ggccgacagt ttttcccttt ggccgcagtt gttggccagg aaggcataaa aactgctctt    420
ttacttggcg cggttgatcg tgaaatcgga gggattgcca tttcaggtcg tagaggcact    480
gcaaaaacag tcatggcgcg agggcttcat gaaatcctcc ctcctattga agttgttgta    540
ggctcaatat caaatgctga cccagcttgt ccagatgagt gggaagatga cttagatgag    600
cgcatagagt acaatgctga caataccatt aagactgaga ttgtcaaatc tcctttcatt    660
cagattccac taggagttac agaagacaga ctcattgggt ctgttgatgt tgaggagtct    720
gtgaaagggg gacaactgt tttccaacct ggtcttttgg ctgaagccca tagaggagtg    780
ttgtatgttg atgaaataaa tctcttagat gagggaatta gtaatttgct tctcaatgta    840
ttgacggatg tgttaatat agttgaaaga gaaggaatca gctttaggca cccgtgcaaa    900
ccacttttaa ttgcaaccta taaccctgaa gaaggtgctg ttcgagagca cttgctagac    960
cgtgttgcca ttaatttaag tgcagaccta cctatgagtt tgaagatcg tgtcgcagca   1020 gttggaattg ccacacagtt tcaggaacgc tgtaatgagg ttttagaat ggtaaatgaa   1080 gagacagaaa cagcaaagac gcagattata ttggctagag aatatttgaa agatgtcaag   1140
ataagtagag agcaattgaa gtatctggtt ttggaagctg tccgaggtgg tgtccaggga   1200
caccgcgccg aattgtatgc agctcgtgtg gcgaagtgtt tagctgcaat tgaaggacga   1260 gaaaagtca caatcgatga cctcagaaag gccgttgagc tggtcattct tcctcgttca   1320
tcactagatg agactccacc tgaacaacaa accaaccac cacctcctcc acctcctcca   1380
caaaatagcg aatctggaga agaagaaaat gaagaagaac aagaagaaga agaagaggat   1440
gaaagcaatg aagaaaatga aaatgagcag caacaggacc aaatacctga agagtttata   1500
tttgacgctg agggcggtct ggtggatgag aaactcctct tctttgctca acaagcccag   1560
aaacgtcggg ggaaagctgg cagggcgaag aatgtcatat tctcagaaga tagaggacgc   1620
tacataaagc caatgcttcc aaagggtcca gtaaaaagat tagctgtgga tgcaacccct   1680
agagcagctg caccatacca gaaattgcgc agagagaagg atatctcagg aactaggaaa   1740
gtctttgttg agaagacaga tatgagggcc aaaagaatgg caaggaaagc tggagccctg   1800
gttatctttg tggttgatgc aagtggcagt atggcattga atcgtatgca aaacgccaaa   1860
ggtgctgcac tcaaactact ggcagagagc tatactagca gggatcaggt ttcgattatt   1920
cctttccgag gggatgctgc ggaagtgctc ttgcccccct ctagatcaat agcaatggca   1980
aggaatcgtc ttgagagact tccttgtggt gtggttctc ctcttgccca tggtttaaca   2040
acggctgtaa gagtaggact taacgcagag aagagtggtg atgtcgggcg cataatgatt   2100
gttgcgataa ccgatggtcg agccaacatt acactgaaaa gatcaactga tccggagtct   2160
attgccccag atgctcctag acccacgtcc aaagaattga aggatgagat tctggaagtt   2220
gctgggaaga tatacaaggc agggatgtct cttctagtga ttgataccga gaacaagttt   2280
gtttcaactg gttttgcaaa ggagatcgca agagttgctc aaggaaaata ttattacttg   2340
ccaaatgctt cggatgctgt aatctcggcc accactaggg atgcactatc tgatctgaag   2400
aattcttgac tcatttttgt ctgcaatacc ttgattctgg atcaaagtgt atattctaat   2460
```

```
tgtgcaacac atcagtcact aaacatgaaa ttataagaaa tgaaattttg ttttaacata    2520
ctcttaaaat gaatttccga ttttattc                                      2548

<210> SEQ ID NO 4
<211> LENGTH: 760
<212> TYPE: PRT
<213> ORGANISM: Arabidopsis thaliana

<400> SEQUENCE: 4

Met Ala Met Thr Pro Val Ala Ser Ser Pro Val Ser Thr Cys Arg
1               5                   10                  15

Leu Phe Arg Cys Asn Leu Leu Pro Asp Leu Leu Pro Lys Pro Leu Phe
                20                  25                  30

Leu Ser Leu Pro Lys Arg Asn Arg Ile Ala Ser Cys Arg Phe Thr Val
            35                  40                  45

Arg Ala Ser Ala Asn Ala Thr Val Glu Ser Pro Asn Gly Val Pro Ala
        50                  55                  60

Ser Thr Ser Asp Thr Asp Thr Glu Thr Asp Thr Thr Ser Tyr Gly Arg
65                  70                  75                  80

Gln Phe Phe Pro Leu Ala Ala Val Val Gly Gln Glu Gly Ile Lys Thr
                85                  90                  95

Ala Leu Leu Leu Gly Ala Val Asp Arg Glu Ile Gly Gly Ile Ala Ile
            100                 105                 110

Ser Gly Arg Arg Gly Thr Ala Lys Thr Val Met Ala Arg Gly Leu His
        115                 120                 125

Glu Ile Leu Pro Pro Ile Glu Val Val Gly Ser Ile Ser Asn Ala
130                 135                 140

Asp Pro Ala Cys Pro Asp Glu Trp Glu Asp Asp Leu Asp Glu Arg Ile
145                 150                 155                 160

Glu Tyr Asn Ala Asp Asn Thr Ile Lys Thr Glu Ile Val Lys Ser Pro
                165                 170                 175

Phe Ile Gln Ile Pro Leu Gly Val Thr Glu Asp Arg Leu Ile Gly Ser
            180                 185                 190

Val Asp Val Glu Glu Ser Val Lys Arg Gly Thr Thr Val Phe Gln Pro
        195                 200                 205

Gly Leu Leu Ala Glu Ala His Arg Gly Val Leu Tyr Val Asp Glu Ile
210                 215                 220

Asn Leu Leu Asp Glu Gly Ile Ser Asn Leu Leu Leu Asn Val Leu Thr
225                 230                 235                 240

Asp Gly Val Asn Ile Val Glu Arg Glu Gly Ile Ser Phe Arg His Pro
                245                 250                 255

Cys Lys Pro Leu Leu Ile Ala Thr Tyr Asn Pro Glu Glu Gly Ala Val
            260                 265                 270

Arg Glu His Leu Leu Asp Arg Val Ala Ile Asn Leu Ser Ala Asp Leu
        275                 280                 285

Pro Met Ser Phe Glu Asp Arg Val Ala Ala Val Gly Ile Ala Thr Gln
    290                 295                 300

Phe Gln Glu Arg Cys Asn Glu Val Phe Arg Met Val Asn Glu Glu Thr
305                 310                 315                 320

Glu Thr Ala Lys Thr Gln Ile Ile Leu Ala Arg Glu Tyr Leu Lys Asp
                325                 330                 335

Val Lys Ile Ser Arg Glu Gln Leu Lys Tyr Leu Val Leu Glu Ala Val
            340                 345                 350

Arg Gly Gly Val Gln Gly His Arg Ala Glu Leu Tyr Ala Ala Arg Val
```

```
              355                 360                 365
Ala Lys Cys Leu Ala Ala Ile Glu Gly Arg Glu Lys Val Thr Ile Asp
    370                 375                 380
Asp Leu Arg Lys Ala Val Glu Leu Val Ile Leu Pro Arg Ser Ser Leu
385                 390                 395                 400
Asp Glu Thr Pro Pro Glu Gln Asn Gln Pro Pro Pro Pro Pro
                405                 410                 415
Pro Pro Gln Asn Ser Glu Ser Gly Glu Glu Asn Glu Glu Gln
            420                 425                 430
Glu Glu Glu Glu Glu Asp Glu Ser Asn Glu Glu Asn Glu Asn Glu Gln
            435                 440                 445
Gln Gln Asp Gln Ile Pro Glu Glu Phe Ile Phe Asp Ala Glu Gly Gly
    450                 455                 460
Leu Val Asp Glu Lys Leu Leu Phe Phe Ala Gln Gln Ala Gln Lys Arg
465                 470                 475                 480
Arg Gly Lys Ala Gly Arg Ala Lys Asn Val Ile Phe Ser Glu Asp Arg
                485                 490                 495
Gly Arg Tyr Ile Lys Pro Met Leu Pro Lys Gly Pro Val Lys Arg Leu
            500                 505                 510
Ala Val Asp Ala Thr Leu Arg Ala Ala Pro Tyr Gln Lys Leu Arg
    515                 520                 525
Arg Glu Lys Asp Ile Ser Gly Thr Arg Lys Val Phe Val Glu Lys Thr
    530                 535                 540
Asp Met Arg Ala Lys Arg Met Ala Arg Lys Ala Gly Ala Leu Val Ile
545                 550                 555                 560
Phe Val Val Asp Ala Ser Gly Ser Met Ala Leu Asn Arg Met Gln Asn
                565                 570                 575
Ala Lys Gly Ala Ala Leu Lys Leu Leu Ala Glu Ser Tyr Thr Ser Arg
            580                 585                 590
Asp Gln Val Ser Ile Ile Pro Phe Arg Gly Asp Ala Ala Glu Val Leu
            595                 600                 605
Leu Pro Pro Ser Arg Ser Ile Ala Met Ala Arg Asn Arg Leu Glu Arg
610                 615                 620
Leu Pro Cys Gly Gly Gly Ser Pro Leu Ala His Gly Leu Thr Thr Ala
625                 630                 635                 640
Val Arg Val Gly Leu Asn Ala Glu Lys Ser Gly Asp Val Gly Arg Ile
                645                 650                 655
Met Ile Val Ala Ile Thr Asp Gly Arg Ala Asn Ile Thr Leu Lys Arg
            660                 665                 670
Ser Thr Asp Pro Glu Ser Ile Ala Pro Asp Ala Pro Arg Pro Thr Ser
            675                 680                 685
Lys Glu Leu Lys Asp Glu Ile Leu Glu Val Ala Gly Lys Ile Tyr Lys
    690                 695                 700
Ala Gly Met Ser Leu Leu Val Ile Asp Thr Glu Asn Lys Phe Val Ser
705                 710                 715                 720
Thr Gly Phe Ala Lys Glu Ile Ala Arg Val Ala Gln Gly Lys Tyr Tyr
                725                 730                 735
Tyr Leu Pro Asn Ala Ser Asp Ala Val Ile Ser Ala Thr Thr Arg Asp
            740                 745                 750
Ala Leu Ser Asp Leu Lys Asn Ser
    755                 760

<210> SEQ ID NO 5
```

<211> LENGTH: 1592
<212> TYPE: DNA
<213> ORGANISM: Arabidopsis thaliana

<400> SEQUENCE: 5

```
ataacccatc caacccaaaa gcatacaata caatgtctac tcttgtttta ttcctccaac      60
ttttttccat cctaccatta gcacttgggt tgaaccaccc aaattgtgac ctgaccaaga     120
ctcaagacca aggctctacc ctaagaatct tccacataga cagcccttgc tcccccttca     180
aatcatcatc cccactctca tgggaagcgc gtgtgctcca gacgctggct caagaccagg     240
cccgtctcca gtacctgagc agcctcgtcg ccgggagatc tgtagtcccc attgcctcag     300
ggcgtcaaat gttgcaaagc actacataca ttgtcaaggc tttgatcggt actccggctc     360
agccgctgct cctagccatg gacacgagca gtgacgtggc ttggattcct tgctccggct     420
gcgttggctg tccttctaac acggcctttt ccctgctaa gtctacatcc ttcaagaacg      480
ttagctgcag cgctcctcag tgtaagcagg taccaaaccc cacgtgtgga gcacgcgcgt     540
gctctttcaa cctcacctat ggaagctcct ccattgcggc taacctctct caagacacga     600
tacgtcttgc cgccgatccg atcaaagcct ttacattcgg atgcgtcaac aaagtcgccg     660
gtggaggaac catcccacca cctcaaggct tgttgggctt gggacgaggc ccactttcac     720
tcatgtcaca ggctcagtct atttacaagt ccacttctc ttactgtttg ccaagtttca      780
ggtctctgac cttctctggt tctctcagac tcggccctac ctcccagccc cagcgcgtga     840
agtacactca acttctcaga aaccctagaa ggtcttctct gtactacgtc aacctcgttg     900
cgatccgcgt tggtcggaaa gtcgtcgatt accgccggc agctattgct tttaatcctt      960
caaccggcgc tggaaccatc ttcgactccg gaactgtgta cacgcggctg gctaaaccgg    1020
tttacgaggc agtgaggaac gagttcagga agcgcgtgaa gccaaccaca gccgtggtga    1080
cgtcactcgg gggtttcgac acgtgctact cagggcaagt caaggtgccg acgataacat    1140
tcatgttcaa gggagtgaac atgacgatgc cggctgataa cctgatgtta cacagtaccg    1200
ccggaagcac gtcgtgcctc gccatggctg cagcgccgga aaacgtaaac tctgtcgtca    1260
atgtgatcgc aagcatgcag cagcagaacc accgtgtcct catcgacgtc cccaatggac    1320
ggctcggttt ggcacgtgaa cgatgctctt agaaagatga atgagacaat aagagcctac    1380
tcatatttat gcagagactt gtttgtttgt gttatttgtg tgtttcattt ttgtcttgtc    1440
ttgcgtcgtt tgcttcacca gtcttagagg gcggaggtgt gtagcatttg tgctatctag    1500
taatttatgt ttttaattgt tcttcaatta tctagagtgt tggatctaag ctaatcaaat    1560
aatgaaacta tattatattt ccttacggta ta                                  1592
```

<210> SEQ ID NO 6
<211> LENGTH: 1350
<212> TYPE: DNA
<213> ORGANISM: Oryza sativa

<400> SEQUENCE: 6

```
atggcgctga gaatgagcat cgcggcgatg tcggtgttgg cggtggcggc ggtgctcgtt      60
gtggccggca cggcggcggc ggcggcggcg tcgtgcccgg cgacgccgcc ggacgcgggg     120
gcgacgctgc agtgtcgca cgcgttcggg ccgtgctcgc cgctgggggc ggagtcggcg      180
gcgccgtcgt gggcggggtt cctggcggac caggcggcgc gcgacgcgtc gaggctgctg     240
tacctcgact cgctggcggt gaaggggcgc gcgtacgcgc cgatcgcgtc ggggaggcag     300
ctgctgcaga cgccgacgta cgtggtgcgc gccccgcctcg gcacgcccgc gcagcagctg     360
```

```
ctcctcgccg tcgacaccag caacgacgcc gcctggatcc cctgctccgg ctgcgcgggc    420
tgccccacct cgtcgccgtt caacccggcc gcctccgcct cctaccgccc ggtgccgtgc    480
ggctcgccgc agtgcgtgct ggcgcccaac ccgtcgtgct cccccaacgc caagtcctgc    540
ggcttcagcc tctcctacgc cgactcctcg ctccaggccg cgctgtcgca ggacaccctc    600
gccgtcgccg cgacgtcgt gaaggcctac accttcggct gcttgcagag gccaccggc     660 acggcggcgc cgccgcaggg cctcctcggg ctcggccgtg gcccgctctc cttcctgtct    720
cagaccaagg acatgtacgg ggccacgttc tcctactgcc tcccgagctt caagtcgctc    780
aacttctccg gcacgctccg gctcggccgg aacgggcagc cgcggcggat caagacgacg    840
ccgctgctcg ccaaccccgca ccgctcgtcg ctctactacg tcaacatgac cggcatccgc    900
gtggggaaaa aggtggtgtc gatcccggcg tccgcgctgg cgttcgaccc ggcgacgggc    960
gccggcacgg tgctcgactc ggggacgatg ttcacgcgcc tggtggcgcc ggtgtacctg   1020
gcgctccgcg acgaggtccg ccgccgcgtc ggcgccggcg ccgccgccgt gtcctccctc   1080
ggcgggttcg acacgtgcta caacaccacg gtggcgtggc cgccggtgac gctgctgttc   1140
gacggcatgc aggtgacgct gccggaggag aacgtggtga tccacaccac gtacggcacc   1200
accagctgcc tggccatggc ggcggcgccc gacggcgtca acacggtgct caacgtcatc   1260
gccagcatgc agcagcagaa ccaccgcgtc ctcttcgacg tgcccaacgg ccgcgtcggc   1320
ttcgcccgcg agagctgcac cgccgcctag                                   1350

<210> SEQ ID NO 7
<211> LENGTH: 1338
<212> TYPE: DNA
<213> ORGANISM: Oryza sativa

<400> SEQUENCE: 7
atgtcactcc ttgcattacc actcctagcc ttcttgtcca tattcttgac tcctacaacg     60
gcagtgagca gctcaacgct gcagctggca cgttctcact cggtgacgcc caatgccggg    120
gcgccgctca gcgcgtgggc cgcgtccgta gccgcccagt cggcggcgga cacggcgcgc    180
atcgtcagca tgctcacgtc gggggcgggg cctctgacga ccagagccaa gcccaaaccc    240
aagaacaggg caaacccacc cgtgccgatc gcgccggggc gtcagatcct cagcatcccg    300
aactacatcg cccgcgcggg cctcggcacg ccggcgcaga cgctcctcgt ggccatcgac    360
cccagcaacg acgcggcgtg ggtgccatgc agcgcctgcg ccggctgcgc cgcctcgtcg    420
ccgtccttct ccccgacgca gtcgtccacg taccgcaccg tgccctgcgg ctcgccgcag    480
tgcgcgcagg tgcccagccc gtcctgcccc gcgggcgtcg gctcctcctg cgggttcaac    540
ctcacctacg cggcgtccac gttccaggcc gtgctcgggc aggactcgct ggccctcgag    600
aacaacgtcg tcgtgtcgta caccttcggg tgcctccgtg tcgtcagcgg caactccgtg    660
ccgccgcagg ggctcatcgg cttcggccgc gggccgctct ccttcttgtc gcagaccaag    720
gacacgtacg gctccgtgtt ctcctactgc ctcccgaact acaggtcgtc taacttctcc    780
ggcacactaa agctcggccc catcgggcaa cccaagagga tcaagacgac gccgttgctc    840
tacaaccctc atcgcccttc actctactac gtcaacatga tcgggatccg cgtcggcagc    900
aaggtcgtgc aagtcccgca atccgcgctc gcgttcaacc cggtcacggg cagcggcacc    960
atcatcgacg ccgggacaat gttcacgcgc cttgccgccc cggtgtacgc cgccgtcgcc   1020
gacgcgttcc ggggcagggt gcgcacgccg gtggcgccgc cgctgggcgg gttcgacacg   1080
```

-continued

| | |
|---|---|
| tgctacaacg tgaccgtctc ggtgcctacc gtcacgttca tgttcgccgg ggcggtcgcc | 1140 |
| gtgacgctgc cggaggagaa cgtgatgatc cacagctcgt cgggcggcgt cgcgtgcctg | 1200 |
| gcgatggccg cggggccctc ggacggcgtg aacgcggcgc tcaatgtgct ggccagcatg | 1260 |
| cagcagcaga accaacgcgt gctgttcgac gtcgccaacg gccgcgtcgg cttctcccgt | 1320 |
| gagctttgca cggcctga | 1338 |

<210> SEQ ID NO 8
<211> LENGTH: 2495
<212> TYPE: DNA
<213> ORGANISM: Nicotiana tabacum

<400> SEQUENCE: 8

| | |
|---|---|
| catctaaaat cctaaatcaa aaacttcgat gctataaaaa tggggttttg ttcaacttca | 60 |
| accctcccac aaacatcact atccaattct caatcttcaa cattcttcac atacttaaaa | 120 |
| ccatgcccaa ttctatcctc cacatattta aggccgaaac ggctaaaatt tcgcctcaga | 180 |
| ataagtgcca ctgcaactat tgattcacct aatggcgctg ttgcagtagt ggaacctgaa | 240 |
| aaacaacctg agaaaatttc ctttggtaga cagtattttc ctctagctgc tgttattgga | 300 |
| caggatgcta ttaaaactgc tcttttactt ggggccattg accgtgagat aggaggaatt | 360 |
| gcaatatgtg ggaagcgtgg aacagcgaaa acgttaatgg cacgtggatt gcatgctatt | 420 |
| ctgccaccaa ttgaagtagt tgttggctca atggcaaatg ctgatccgaa ctgtcccgat | 480 |
| gagtgggaag acgggctagc tgacagagca gaatatgggt ctgatggtaa tatcaagacc | 540 |
| cagatagtta aatccccatt tgttcagatt ccccttggtg tcacagaaga tagattgatt | 600 |
| ggctctgttg atgtcgagga gtccgtgaaa tctggaacca ctgtcttttca accaggcctc | 660 |
| ctcgcagaag ctcatcgagg agttctatat gttgatgaga ttaatctatt agatgaaggt | 720 |
| ataagtaacc tacttctgaa tgtattgact gagggagtca atattgtaga agagagggga | 780 |
| atcagctttc gacatccatg caaaccacta ctaattgcta cctataaccc tgaagagggt | 840 |
| gcggttcgtg agcatctgct agaccgtatt gcgattaatt taagtgcaga tcttccaatg | 900 |
| agttttgacg atcgtgttgc agctgttgac atagcaacac gttttcagga gtgtagcaat | 960 |
| gaggttttta aaatggtgga tgaagaaaca gacagtgcaa aaacccagat aatattggca | 1020 |
| agggagtatt taaggatgt cacaatcagt agagatcaac taaaatactt ggtcatggaa | 1080 |
| gcaattcgtg gtggctgcca ggggcaccga gctgaacttt atgctgctcg tgtagccaaa | 1140 |
| tgcttagctg ccatcgatgg acgtgaaaaa gttggtgttg atgagctgaa aaaagctgta | 1200 |
| gagcttgtca tcctcccacg ttcaactata gttgaaaacc caccagacca gcaaaaccag | 1260 |
| cagccaccctc ctcccctcc ccctcccaa atcaagatt cttcagaaga gcagaatgaa | 1320 |
| gaagaagaaa aagaagaaga agatcaagag gatgagaaag atagagaaaa tgaacagcaa | 1380 |
| cagccacaag tccctgatga gtttatttt gatgcgaag gtggtttagt ggatgaaaaa | 1440 |
| cttctcttct ttgcacaaca agcacaaaga cgcaaaggaa aagctggacg agcaagaag | 1500 |
| gtcatctttt ccgaagatag aggtcgatat ataaagccaa tgcttccaaa gggtccagtg | 1560 |
| aagagattgg cagttgatgc aactctaaga gcagcggcac catatcagaa gttacgaaga | 1620 |
| gcaaaggaca tccaaaaaac tcgcaaggtt tatgtagaga aaactgacat gagagccaaa | 1680 |
| agaatggcac gcaaagccgg agctctggtg atattcgtag ttgacgctag tgggagtatg | 1740 |
| gcactgaata gaatgcagaa tgccaaagga gcagcactta aactacttgc agagagttat | 1800 |
| acaagcagag atcaggtctg tatcattccc ttccgcggag atgctgctga agttttgttg | 1860 |

```
ccaccttcta ggtcaatatc gatggcaaga aatcgtcttg agagacttcc ctgtggaggg    1920
ggttctcccc ttgctcatgg gcttacgacg gcagttagag ttggaatgaa tgcagaaaag    1980
agtggtgatg ttggacgtat catgattgtt gcaattactg atggtagagc taacatctct    2040
cttaaaagat ccacagaccc tgaagctgaa gcttctgatg cacccagacc ttcttcccaa    2100
gagctgaagg atgagattct cgaggtggct ggtaaaatat acaaaacagg aatgtctctc    2160
ctcgtcatag atacagaaaa taagtttgtt tctactggtt ttgcgaaaga aatcgcgaga    2220
gtagctcaag ggaagtacta ttatttacca aatgcttcag atgctgtgat atctgcagca    2280
acaaaggatg cattatctgc attaaaggaa tcttgaccta aactcgatcg aattaattgt    2340
aaatgttgtt ttgagtatag attattggga ggatataaga gcttgcttga taattcttat    2400
cttttgttgt actaattgaa cttatttctc aattatgcaa tcagggtaat gaagattctt    2460
ttcatttcaa aaaaaaaaa aaaaaggaa ttcga                                  2495

<210> SEQ ID NO 9
<211> LENGTH: 2607
<212> TYPE: DNA
<213> ORGANISM: Pisum sativum

<400> SEQUENCE: 9
gtggcaccgt gatcgttggt tctaaattca atcaaatggg tttcagtttg acacacacac      60
ctcacaccac tgcttccccc aatcttcaac tccgatttca ctctcttctt cctccttcat    120
tcacatcaca accgtttctc tctttgcatt ccacatttcc accaaaacgc accgttccaa    180
aacttcgcgc tcaatccgaa aatggagctg ttctgcaagc ttctgaggag aagctcgatg    240
cttccaatta cggaagacag tacttccctc tcgctgctgt tataggccaa gatgctatta    300
aaactgctct tttacttggg gctactgacc ctaggattgg agggattgct atatcaggaa    360
ggcggggaac tgctaaaaca ataatggcgc gtggaatgca tgcaattctt ccgcctattg    420
aagttgtaca aggttccatt gccaatgcag atccctcgtg ccctgaagag tgggaagatg    480
gtctttacaa acgcgtggaa tatgattctg atggaaatgt taaaactcat atcatcaagt    540 ctcctttttgt tcagattcct cttggagtca cagaggacag actcattgga tcagttgatg    600
ttgaggagtc tgtgaagaca ggcacaactg ttttccaacc aggcctactc gctgaagctc    660
atagaggtgt tttatatgtt gatgaaatta atcttttgga cgagggtatc agtaatttgc    720
tccttaatgt actgactgaa ggagtaaata ttgttgaaag agagggaatc agctttaggc    780
acccatgcag gccccttctg attgctacct ataaccctga cgaaggttct gttcgtgaac    840
atctgctaga ccgcattgca attaatttga gtgcagatct tccaatgagt tttgaaaacc    900
gtgttgaagc tgttggaatt gcaacagaat tcaggataa ctgtggccaa gtatttaaaa    960
tggttgatga ggatacagac aatgcaaaga cacagatcat cttggctaga gagtatctca    1020
aggatgttac tattagcaaa gaacaattaa aatacctggt tatcgaggct ttacgaggtg    1080
gtgtccaggg acacagagct gagctgtatg ctgctcgtgt tgctaagtgc ttagctgctc    1140
tggagggacg tgaaaaggtt tatgtggatg accttaaaaa agccgtagaa ttggtcattc    1200
ttccccggtc aatcattacc gatactccac ctgagcaaca aaatcaacct cctccgccac    1260
caccgcctcc acaaaaccaa gaatctaatg aagaacagaa tgaagaggaa gaacaagaag    1320
aagaggaaga ggatgacaat gatgaagaga tgaacaacaa gcaagaccaa ttacctgaag    1380
aatttatctt tgatgctgaa gggggtttgg tggatgaaaaa acttctcttc tttgcccaac    1440
```

-continued

```
aagcacagag acgccgtggg aaggctggaa gggcaaaaaa tgtcatatttt tcagaggaca      1500 gaggccgata catcaagcca atgcttccaa agggtcctgt aaagagatta gcagttgatg      1560
caacccttag agctgctgca ccttatcaaa agttgcgaag ggaaaaagac accgaaaacc      1620
gtagaaaagt atatgttgaa aaaactgaca tgagggcaaa gagaatggcg cgtaaagcag      1680
gagcattggt catatttgtg gttgatgcta gtggaagcat ggcattgaac agaatgcaga      1740
atgcaaaagg tgcggcactt aagcttctgg cagaaagtta tacaagcagg gatcaggtat      1800
ctataattcc attccgtgga gattctgcag aagttctcct accaccttct agatcaattg      1860
caatggcaag gaaacgtctt gaaagactgc catgtggtgg agggtcgccc cttgcacatg      1920
gtcttaccac agctgttagg gttggattaa atgcagagaa aagtggtgat gttggacgta      1980
taatgattgt tgcaatcact gatggtcgtg ccaacatatc attgaaaagg tcaaatgacc      2040
ctgaagctgc tgccgctagt gatgcccta aacctacatc gcaagaatta aaggatgaaa       2100
ttattgaggt cgctgcgaag atatataaaa caggaatgtc tctccttgtc atcgacactg      2160
aaaacaagtt tgtgtcaact ggtttcgcta agagattgc tagagttgct caagggaagt       2220
attattattt gccaaatgct tctgacgcag ttgtctcgtt ggcaacaagg gaagctttag      2280
cagctctgaa gagttcatga aactgaatga gaagcaacca atcttgacac ccctcccaat      2340 tttttgttaca aatgttatt gtaaattgcg caactataaa tgtctggtgg gaagaaagca      2400
tactcttata gcaagttcca ttatttccta ttttcgatga gattttgttt ttagtttctg      2460
tgtggattgt tgtaagtata aatttctctt actagtagac tcttcgaagt cagtcactaa      2520
ctgttaggag ggtggactcg gctggacaat taatttttcac acaactttat aaataaatta    2580 gaatctttg taaagaaaaa aaaaaaa                                           2607
```

<210> SEQ ID NO 10
<211> LENGTH: 2571
<212> TYPE: DNA
<213> ORGANISM: Oryza sativa

<400> SEQUENCE: 10

```
gaccgcgctc tctccctccc ctcccatggc gatggccacc accgcgctct ccgcctccct       60
cccgcgccta ctcccgcctc gccgccgccg cttcccgacg ccctcctcct cctcccctc      120 cgccgcatcc acctccacct cccgcgtcgt ccgcctgcgg gccgccgcgg cctcggcgcc     180
atccgaggtc ctcgactcca ccaacggggc catcccctcg ggaagggcg gcggcgggca      240 gcagtacggg agggagtatt tccccttggc cgctgtcgtc gggcaggatg caattaaaac      300
tgctctgctg cttggggcaa ttgaccgtga aattggaggc atcgccatct cagggaagcg      360
tgggacagca aagacagtga tggctcgtgg cttgcacgct atgcttccac ctattgaagt      420
ggttgtaggc tcgattgcaa atgctgaccc taactaccca gaagaatggg aggagggttt      480
ggctaaccaa gttcaatatg atgctgatgg taacttgaag accgagatta tcaaaacacc      540
ttttgtgcag atcccgcttg gtatcactga ggataggtta atcggatcag tcgatgttga      600
agcatctgtg aaatcaggaa ctactgtgtt tcaacctggc cttcttgctg aagctcacag      660
aggcgttctt tatgttgatg agataaatct attggatgag ggcgtaagca atctacttct      720
gaatgtcttg actgagggag tcaatattgt ggaaagagag gcattagct ttcgtcatcc       780 atgcaaacca cttctaattg ctacttacaa cccagaggaa ggatctgtac gtgaacactt      840
acttgatcgt attgcaatta atttaagcgc tgatctgcca atgagtttg atgatcgtgt       900 ggcagctgtg gatattgcaa cacaatttca agagtccagc aaagaggttt ttaaaatggt      960
```

-continued

```
ggaagaagaa actgaggttg caaaaaccca gataattttg gcaagagaat atctgaaaga    1020
tgttgcaatc agcacagagc agctcaaata tcttgtcatg gaagctatac gcggtggctg    1080
tcaggggcac cgggctgagc tgtatgctgc tcgagtggca aaatgtcttg ctgctatgga    1140
agggcgtgaa aaagtatatg tggatgacct taagaaagct gtagagctag ttattctacc    1200
tcgatcaatc ctatctgata acccacagga gcagcaagac caacaacctc ctccaccccc    1260
accgccaccc cctccacaag atcaagattc tcaagaagat caagatgaag acgaggaaga    1320
ggaccaagag gacgatgatg aagaaaatga acagcaggac cagcagatac ctgaggagtt    1380 cattttgat gctgaaggtg gtatagtaga tgagaagctc cttttctttg ctcagcaagc    1440
tcaaagacgg cgagggaaag ctggacgagc aaagaatctc atattctcat ctgataggg    1500 acgatacata ggttctatgc ttcccaaggg tccaataagg aggttagctg ttgatgccac    1560
acttcgagca gctgcaccat accagaaact gaggagagag aaagatcgtg acaagacaag    1620
aaaggttttt gttgaaaaaa ctgacatgag agccaaaaga atggctcgaa aagcaggcgc    1680
actggtcata tttgttgtgg atgctagcgg tagcatggct ctgaatcgca tgcagaatgc    1740
gaaaggtgca gcattaaagt tgcttgcaga aagctacaca agcagagatc aggtttcaat    1800
cattccattt cgtggagatt ttgctgaggt tcttcttcca ccttcaagat ccatagcaat    1860
ggcccgcaat cgtcttgaga agttaccatg tggtggcggt tctcctttag ctcacggcct    1920
tagcacagct gtcagagtgg gtttgaatgc tgaaaagagc ggtgatgttg acgtatcat    1980 gattgttgca atcaccgatg gaagagctaa tgtgtcactg aagaaatcga ctgacccaga    2040
agccacttca gatgctccaa gaccttcttc tcaagaatta aaggatgaga tacttgaggt    2100
ggctggcaaa atatacaagg ctggaatttc acttcttgtt attgataccg agaacaagtt    2160
tgtatccaca ggatttgcca aggaaattgc aagggtcgcc caaggtaaat actattacct    2220
gccgaatgct tcagacgctg ttatttccgc cgccaccaag actgcactct cggacctgaa    2280
gagttcgtga tcctggagag cgttttacct tcagataatg agtggttttt accttttacc    2340
ttgtttggtg cagcagtgtc catgtttcgt gtaactttgg gacgtttcgg ctgtgataac    2400
caattttggc ataggatttt taccgtgaga gttggaattc gggcgtagca ccgtgtaaag    2460
aatcatataa tccctcttct gtctaaataa ttggccatgt aaatatggtg ttattgcgta    2520
cagttctaag taataataac attcataatt tatgtgaaga aagaaattgc              2571
```